United States Patent [19]
Fodstad et al.

[11] Patent Number: 5,877,308
[45] Date of Patent: Mar. 2, 1999

[54] CAPL-SPECIFIC OLIGONUCLEOTIDES AND METHODS OF INHIBITING METASTATIC CANCER

[75] Inventors: Oystein Fodstad; Eivind Hovig, both of Oslo; Olav Engebraaten, Lørenskog; Gunhild Maelandsmo, Oslo, all of Norway; Sudhir Agrawal, Shrewsbury; Eric von Hofe, Wellesley, both of Mass.

[73] Assignees: Hybridon, Inc., Cambridge, Mass.; Norwegian Radium Hospital Research Foundation, Oslo, Norway

[21] Appl. No.: 642,407

[22] Filed: May 3, 1996

Related U.S. Application Data

[60] Division of Ser. No. 602,036, Feb. 16, 1996, which is a continuation-in-part of Ser. No. 391,375, Feb. 19, 1995.

[51] Int. Cl.[6] .............................. C07H 21/00; C12N 5/10; C12Q 1/68
[52] U.S. Cl. .................... 536/24.5; 536/24.3; 536/24.31; 536/24.33; 435/6; 435/172.1; 435/172.3; 435/320.1; 435/375
[58] Field of Search .................................. 536/24.5, 24.3, 536/24.31, 24.33; 435/6, 91.1, 91.3, 91.31, 91.4, 172.3, 240.2, 320.1, 375; 935/3, 5, 8, 33, 34

[56] References Cited

FOREIGN PATENT DOCUMENTS

WO 92/00757 1/1992 WIPO .
WO 95/20656 8/1995 WIPO .

OTHER PUBLICATIONS

E. Uhlmann et al. Chem. Reviews 90(4) 543–584 ('90).
P. Westermann et al. Biomed. Biochim Aero 48(1) 85–93 ('89).
W. James Antiviral Chem & Chemotherapy 2(4) 191–214 ('91).
R. Stoll et al. Pharmaceut. Res. 12(4) 465–83 ('95).
Cairns (1981) *Nature* 289:353–57.
Nicolson (1982) *Biochim. Biophys. Acta* 695:113–176.
Nicolson (1984) *Cancer Metast. Rev.* 3:24–42.
Klein et al. (1985) *Nature* 315:190–195.
Nicolson (1987) *Cancer Res.* 47:1473–1487.
Berger et al. (1988) *Cancer Res.* 48:1238–1243.
Ebralidze et al. (1989) *Genes Dev.* 3:1086–1093.
Kjonniksen et al. (1990) *J. Nat. Cancer Inst.* 82(5) Mar.
Monocrief (1990) *J. Mol. Evol.* 30:522–562.
Heizmann et al. (1991) *TIBS* 16:98–103.
Hilt et al. in *Novel Calcuim–binding Proteins* (Heizmann, C.W., ed.) Springer–Verlag, Berlin, 1991, pp. 65–103.
Engelkamp et al. (1992) *Biochem.* 31:10258–10264.
Engebraten in *Biology and Experimental Therapy of Invasive glioma cells in tissue culture,* The Gade Institute, Department of Pathology, University of Berger, Norway (1992).
Lee et al. (1992) *Proc. Natl. Acad. Sci.* (USA) 89:2504–2508.
Davies et al. (1993) *Oncogene* 8:999–1008.
Engelkamp et al. (1993) *Proc. Natl. Acad. Sci.* (USA) 90:6547–6551.
Stein et al. (1993) *Science* 261:1004–1012.
Tulchinsky et al. (1993) *Oncogene* 8:79–86.
Kriajevska et al. (1994) *J. Biol. Chem.* 269:19679–19682.
Wagner (1994) *Nature* 372:333–335.
Kligman et al. (1988) *TIBS* 13:437–442.
Engelkamp et al. (1993) *Proc. Natl. Acad. Sci. USA* 90:6547–6551.
Agrawal (1992) *Trends in Biotech.* 10:152.
Maelandsmo et al. (1995) *Cancer Research* 55:2884.
James (1991) *Antiviral Chemistry & Chemotherapy* 2:191–214.
Milligan et al. (1993) *Journal of Medicinal Chemistry* 36:1923–1937.
Rojanasakul (1996) *Advanced Drug Delivery Reviews* 18:115–131.

Primary Examiner—Charles C.P. Rories
Attorney, Agent, or Firm—Hale and Dorr LLP

[57] ABSTRACT

Disclosed are synthetic oligonucleotides having a nucleotide sequence complementary to CAPL nucleic acid. Also disclosed are methods of inhibiting the expression of CAPL gene and methods of inhibiting metastatic cancer using CAPL-specific oligonucleotides.

6 Claims, 7 Drawing Sheets

FIG. 1A

MELANOMA

SARCOMA

CAPL-SPECIFIC OLIGONUCLEOTIDES AND METHODS OF INHIBITING METASTATIC CANCER

CROSS-REFERENCE TO RELATED APPLICATIONS

This application is a divisional of co-pending application Ser. No. 08/602,036 filed on 16 Feb. 1996, which is a continuation-in-part of application Ser. No. 08/391,375 filed 17 Feb. 1995.

FIELD OF THE INVENTION

The present invention relates to cancer therapy. More particularly, this invention relates to the use of synthetic oligonucleotides to control and treat metastatic cancer.

BACKGROUND OF THE INVENTION

Tumor progression is thought to occur when variant cells having selective growth properties arise within a tumor cell population (Foulds (1975) *Neoplastic Dev.*, Vol. 2, Academic Press, London). One of the final stages of tumor progression is the appearance of the metastatic phenotype (Nicolson (1984) *Cancer Metast. Rev.* 3:24–42). During metastasis, the tumor cells invade the blood vessels, survive against circulating host immune defenses, and then extravasate, implant, and grow at sites distant from the primary tumor (Nicolson (1982) *Biochim. Biophys. Acta* 695:113–176; and Nicolson (1987) *Cancer Res.* 47:1473–1487). This ability of tumor cells to invade neighboring tissues and to colonize other organs is among the leading causes of cancer-related deaths.

The term metastasis encompasses a number of phenotypic traits which together result in the clinical problem that most often leads to death from cancer. The cells lose their adherence and restrained position within an organized tissue, move into adjacent sites, develop the capacity both to invade and to egress from blood vessels, and become capable of proliferating in unnatural locations or environments. These changes in growth patterns are accompanied by an accumulation of biochemical alterations which have the capacity to promote the metastatic process.

Metastatic cancer may invade many different regions of the body, bone being one of the most frequent sites. For example, the metastases from carcinomas and occasionally even from sarcomas are known to spread to the skeleton. Skeletal metastases may be silent or produce symptoms by the same mechanisms as primary tumors, i.e., pain, swelling, deformity, encroachment on hematopoietic tissue in the bone marrow, compression of spinal cord or nerve roots, and pathologic fractures. In addition, rapidly lytic skeletal metastases can result in hypercalcemia. Because of the painful and often debilitating effects of such metastases, better treatment and improved regimens are urgently needed.

So far, little is known about the intrinsic mechanism involved in the metastatic cascade. It is likely that in some cases the augmented metastatic potential of certain tumor cells may be due to an increased expression of oncogenes, which normally are responsible for control of various cellular functions, including differentiation, proliferation, cell motility, and communication (Cairns (1981) *Nature* 289:353–57; Berger et al. (1988) *Cancer Res.* 48:1238–1243; and Klein et al. (1985) *Nature* 315:190–195).

In recent years, several genes postulated to be involved in this process have been identified. For example, some members of the S100 family of $Ca^{2+}$-binding proteins may have relevance to different aspects of neoplastic progression, tumorigenicity, and metastatic potential (Ebralidze et al. (1989) *Genes & Dev.* 3:1086–1092; Lee et al. (1992) *Proc. Natl. Acad. Sci.* 89:2504–2508)). This family consists of 13 human members expressed in a tissue- and cell-specific manner. These proteins have been found in various human tumors such as virtually all primary and metastatic melanomas, and have been used as a marker for the identification of tumor histopathogenesis (see, e.g., Lee et al. (1992) *Proc. Natl. Acad. Sci.* (*USA*) 89:2504–2508). The normal cellular functions of the S100-proteins have not been clarified, although several have been suggested, including involvement in essential signal transduction pathways, regulation of cell growth and differentiation, and participation in cytoskeletal organization (Kligman et al. (1988) *Trends. Biol. Sci.* 13:437–443).

One particular human S100 protein has been found to be encoded by the CAPL gene localized to chromosome 1 (Iq2–22) together with at least five other structurally related genes. (Englekamp et al. (1992) *Biochem.* 31:10258–10264; Engelkamp et al. (1993) *Proc. Natl. Acad. Sci.* (*USA*) 90:6547–6551). Its murine counterpart, mts1 is expressed in metastatic murine mammary carcinoma (Ebralidz et al. (1989) *Genes Dev.* 3:1086–1093). These genes, encoding small (10 kD) $Ca^{2+}$-binding proteins of the S100-family, share a high degree of homology, particularly in regions that encode the $Ca^{2+}$-binding domains (Moncrief (1990) *J. Mol. Evol.* 30:522–562.

The mechanism by which cancer becomes metastatic, as well as the function of the S100-related genes and proteins in the progression of metastatic cancer has yet to be elucidated. A better understanding of these underlying processes will provide more effective methods of treating and controlling metastatic cancer which are surely needed, including methods of inhibiting the expression of genes involved in the progression of the disease.

SUMMARY OF THE INVENTION

The present invention provides methods and compositions for treating and controlling metastatic cancer. These compositions and methods were developed based on the present discovery that CAPL is expressed at high levels in most osteosarcoma tumor tissue and in established osteosarcoma cell lines compared to the levels observed in other tumor types. It has also been discovered that a ribozyme specific for a CAPL transcript reduced CAPL expression in, decreased the proliferation rate of, and changed the morphology of, a human metastatic cancer cell line into which the ribozyme had been transfected. In addition, this ribozyme effectively reduced the development of bone metastases in mammalian animal models injected with human osteosarcoma cells transfected with the ribozyme.

These discoveries have been exploited to produce the present invention which, in a first aspect, includes synthetic oligonucleotides having a nucleotide sequence complementary to CAPL nucleic acid.

For purposes of the invention, the term "synthetic oligonucleotide" is meant to include chemically synthesized polymers of six or more nucleotides or nucleotide analogs connected together via at least one 5' to 3' internucleotide linkage. This linkage may include any linkages that are known in the antisense art. Such molecules have a 3' terminus and a 5' terminus.

The term "oligonucleotide having a nucleotide sequence complementary to a nucleic acid" is intended to encompass an oligonucleotide sequence of six to about 50 nucleotides in length that binds to the nucleic acid under physiological conditions, e.g., by Watson-Crick base pairing (interaction between oligonucleotide and single-stranded nucleic acid) or by Hoogsteen base pairing (interaction between oligonucleotide and double-stranded nucleic acid) or by any other means including in the case of a oligonucleotide binding to RNA, pseudoknot formation. Such binding (by Watson-Crick base pairing) under physiological conditions is measured as a practical matter by observing interference with the function of the nucleic acid sequence.

In some embodiments, the oligonucleotides of the invention include the trinucleotide GUC (SEQ ID NO:2). In other embodiments, the claimed oligonucleotide has a nucleotide sequence complementary to a CAPL transcript including exon 2 or including a transcriptional start site, a translational start site, a translational stop site, or a splice site. In preferred embodiments, this nucleotide sequence is complementary to a CAPL transcript including at least a portion of exon 2 that contains nucleotide 132. In particular embodiments, the invention includes a synthetic oligonucleotide having SEQ ID NQ:9 or NO:10, which is complementary to a region on CAPL nucleic acid to which a CAPL-specific ribozyme binds, (and which may include the "GUX" sequence), an oligonucleotide having SEQ ID NO:3 or 4 (which is complementary to a 3' splice site), an oligonucleotide having SEQ ID NO:5 or 6 (which is complementary to a 5' splice site), or an oligonucleotide having SEQ ID NO:7 or 8 (which is complementary to the translational start site).

A modified oligonucleotide also encompasses those that are linked by at least one "non-phosphodiester-internucleotide bond, i.e., a linkage other than a phosphodiester between the 5' end of one nucleotide and the 3' end of another nucleotide in which the 5' nucleotide phosphate has been replaced with any number of chemical groups. Preferable synthetic linkages include alkylphosphonates, phosphorothioates, phosphorodithioates, alkylphosphonothioates, phosphoramidates, phosphoramidites, phosphate esters, carbamates, carbonates, phosphate triesters, acetamidate, and carboxymethyl esters. Any of these linkages may also be substituted with various chemical groups, e.g., an aminoalkylphosphonate. In one preferred embodiment of the invention, all of the nucleotides of the oligonucleotide comprises are linked via phosphorothioate and/or phosphorodithioate linkages.

In some embodiments of the invention, the oligonucleotides are modified. As used herein, the term "modified oligonucleotide" encompasses oligonucleotides with modified nucleic acid(s), base(s), and/or sugar(s) other than those found in nature. For example, a 3', 5'-substituted oligonucleotide is an oligonucleotide having a sugar which, at both its 3' and 5' positions is attached to a chemical group other than a hydroxyl group (at its 3' position) and other than a phosphate group (at its 5' position).

For purposes of the invention, the term "2'-substituted oligonucleotide" refers to an oligonucleotide having a sugar attached to a chemical group other than a hydroxyl group at its 2' position. The 2'-OH of the ribose molecule can be substituted with -O-lower alkyl containing 1–6 carbon atoms, aryl or substituted aryl or allyl having 2–6 carbon atoms, e.g., 2'-O-allyl, 2'-O-aryl, 2'-O-alkyl (such as a 2'-O-methyl), 2'-halo, or 2'-amino, but not with 2'-H, wherein allyl, aryl, or alkyl groups may be unsubstituted or substituted, e.g., with halo, hydroxy, trifluoromethyl, cyano, nitro, acyl, acyloxy, alkoxy, carboxyl, carbalkoxyl or amino groups.

A modified oligonucleotide may also be one with added substituents such as diamines, cholesteryl, or other lipophilic groups, or a capped species. In addition, unoxidized or partially oxidized oligonucleotides having a substitution in one nonbridging oxygen per nucleotide in the molecule are also considered to be modified oligonucleotides. Also considered as modified oligonucleotides are oligonucleotides having nuclease resistance-conferring bulky substituents at their 3' and/or 5' end(s) and/or various other structural modifications not found in vivo without human intervention are also considered herein as modified.

In other embodiments of the invention, the CAPL-specific synthetic oligonucleotide includes at least one ribonucleotide, at least one deoxyribonucleotide, or both ribonucleotide(s) and deoxyribonucleotide(s). In most preferred embodiments, the oligonucleotide of the invention has a length of about 15 to 30 nucleotides.

In another aspect of the invention, a method of inhibiting the expression of a CAPL gene is provided. In this method, CAPL nucleic acid is contacted with a synthetic oligonucleotide complementary to the CAPL nucleic acid.

In yet another aspect of the invention, a method of treating or inhibiting metastatic cancer such as osteosarcoma is provided. In this method, a therapeutic amount of a synthetic oligonucleotide complementary to CAPL nucleic acid is administered to a subject afflicted with cancer. In one embodiment, at least two different synthetic oligonucleotides are administered simultaneously, each having a nucleotide sequence complementary to CAPL nucleic acid, but the nucleic acid sequences of the oligonucleotides being different.

The methods of the invention also provide a means of examining the function of the CAPL gene in a control animal and in an animal afflicted with metastatic cancer. Presently, gene function can only be examined by the arduous task of making a "knock out" animal such as a mouse. This task is difficult, time-consuming and cannot be accomplished for genes essential to animal development since the "knock out" would produce a lethal phenotype. The present invention overcomes the shortcomings of this model.

A therapeutic formulation is also provided which includes at least one CAPL-specific synthetic oligonucleotide of the invention and a pharmaceutically and physiologically acceptable carrier.

BRIEF DESCRIPTION OF THE DRAWINGS

The foregoing and other objects of the present invention, the various features thereof, as well as the invention itself may be more fully understood from the following description, when read together with the accompanying drawings in which:

FIG. 1A is a representation of the genomic sequence of the human CAPL gene, wherein lower case letters indicate regions of the gene that are spliced out in the mRNA, and "n" refers to undetermined bases;

DETAILED DESCRIPTION OF THE PREFERRED EMBODIMENTS

The patent and scientific literature referred to herein establishes the knowledge that is available to those with skill in the art. The issued U.S. patent and allowed applications cited herein are hereby incorporated by reference.

The present invention provides synthetic antisense oligonucleotides specific for CAPL nucleic acid which are useful in treating metastatic cancer.

Antisense oligonucleotide technology provides a novel approach to the inhibition of CAPL expression, and hence, to the treatment or prevention of metastatic cancer (see generally, Agrawal (1992) *Trends in Biotech.* 10:152; Wagner (1994) *Nature* 372:333–335; and Stein et al. (1993) *Science* 261:1004–1012). By binding to the complementary nucleic acid sequence (the sense strand), antisense oligonucleotides are able to inhibit splicing and translation of RNA. In this way, antisense oligonucleotides are able to inhibit protein expression. Antisense oligonucleotides have also been shown to bind to genomic DNA, forming a triplex, and inhibit transcription. Furthermore, a 17mer base sequence statistically occurs only once in the human genome, and thus extremely precise targeting of specific sequences is possible with such antisense oligonucleotides.

Figure 1B:
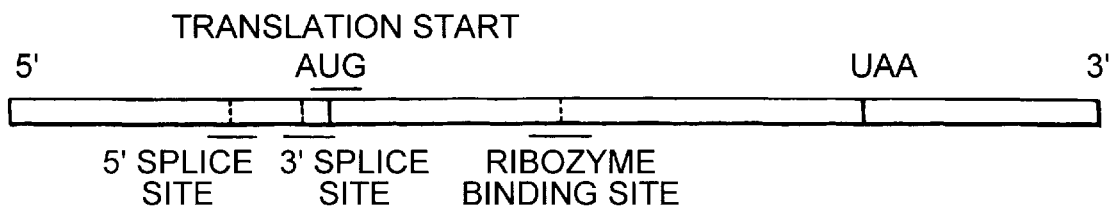
FIG. 1B is a diagrammatic representation of the unspliced CAPL RNA including areas to which useful oligonucleotides of the invention may be targeted.

The oligonucleotides of the invention include any oligonucleotides that inhibit CAPL gene expression, and are directed to a portion of the human CAPL nucleic acid sequence, which is known (Engelkamp et al. (1993) *Proc. Natl. Acad. Sci. (USA)* 90:6547–6551 GenBank, Ac. No. 218950), shown schematically in FIG. 1A, and is set forth as SEQ ID NO:1. These targeted regions include, but are not limited to, any portions of known exons, as well as splice sites (exon-intron boundaries), ribozyme binding sites, transcriptional start sites, translational start sites, or translational stop sites.

The nucleotide sequences of some representative, non-limiting oligonucleotides specific for human CAPL are listed below in TABLE 1.

TABLE 1

| TARGETED SITE | SEQUENCE (5'→3') | SEQ ID NO: |
|---|---|---|
| 3' splice site | GTCAGGATCTGGGAGCAGGAGG | 3 |
| 3' splice site | GUCAGGAUCUGGGAGCAGGAGG | 4 |
| 3' splice site | GTCAGGATCTGGGAGCAGGAG | 23 |
| 5' splice site | CACAACTCACCAAACCAAGAAA | 5 |
| 5' splice site | CACAACUCACCAAACCAAGAAA | 6 |
| translation start | CAGAGGGCACGCCATGACAGC | 7 |
| translation start | CAGAGGGCACGCCAUGACAGC | 8 |
| translation start | GCCATGACAGCAGTCAGGAT | 22 |
| ribozyme site | GGAAGGTGGACACCATCACA | 9 |
| ribozyme site | GGAAGGUGGACACCAUCACA | 10 |

In accordance with the disclosure provided herein, those of skill in the art can identify, with only a minimum of experimentation, other antisense nucleic acid sequences that inhibit CAPL expression. For example, other sequences targeted specifically to CAPL can be selected using an RNase H cleavage assay (Frank et al. (1993) *Proc. Int. Conf. Nucleic Acid Med. Applns.* 1:4.14 (abstract)) and a random, e.g., 20mer, library from which human CAPL cDNA is transcribed and used in the assay. This RNase H analysis procedure indicates those regions within the CAPL mRNA that are most susceptible to antisense binding.

The synthetic oligonucleotides of the invention are composed of ribonucleotides, deoxyribonucleo-tides, or a combination of both, with the 5' end of one nucleotide and the 3' end of another nucleotide being covalently linked. These oligonucleotides are at least 6 nucleotides in length, but are preferably 12 to 50 nucleotides long, with 15 to 30 nucleotides being the most common.

These RNA-, DNA-, and RNA/DNA-containing oligonucleotides can be prepared by the art recognized methods such as phosphoramidate or H-phosphonate chemistry which can be carried out manually or by an automated synthesizer (see, e.g., Uhlmann et al. (*Chem. Rev.* (1990) 90:534–583).

The oligonucleotides of the invention may also be modified in a number of ways without compromising their ability to hybridize to CAPL nucleic acid. For example, the oligonucleotides may contains other than phosphodiester internucleotide linkages between the 5' end of one nucleotide and the 3' end of another nucleotide in which the 5' nucleotide phosphate has been replaced with any number of chemical groups. Examples of such chemical groups include alkylphosphonates, phosphorothioates, phosphorodithioates, alkylphosphonothioates, phosphoramidates, phosphate esters, carbamates, acetamidate, carboxymethyl esters, carbonates, and phosphate triesters. Oligonucleotides with these linkages can be prepared according to known methods (reviewed in *Protocols for Oligonucleotides and Analogs, Meth. Mol. Biol.*, Vol. 20 (Agrawal, ed.) Humana Press, Totowa, N.J. (1993) and Uhlmann et al. (1990) *Chem. Rev.* 90:543–583).

Other modifications include those which are internal or at the end(s) of the oligonucleotide molecule and include additions to the molecule of the internucleoside phosphate linkages, such as cholesteryl or diamine compounds with varying numbers of carbon residues between the amino groups and terminal ribose, deoxyribose and phosphate modifications which cleave, or crosslink to the opposite chains or to associated enzymes. Examples of such modified oligonucleotides include oligonucleotides with a modified base and/or sugar such as 2'-O-alkylated ribose, arabinose instead of ribose, or a 3', 5'-substituted oligonucleotide having a sugar which, at both its 3' and 5' positions is attached to a chemical group other than a hydroxyl group (at its 3' position) and other than a phosphate group (at its 5' position). Other modified oligonucleotides are capped with a nuclease resistance-conferring bulky substituent at their 3' and/or 5' end(s), or have a substitution in one nonbridging oxygen per nucleotide. Such modifications can be at some or all of the internucleoside linkages, as well as at either or both ends of the oligonucleotide and/or in the interior of the molecule.

The preparation of these modified oligonucleotides is well known in the art (reviewed in Agrawal et al. (1992) *Trends Biotechnol.* 10:152–158). For example, nucleotides can be covalently linked using art-recognized techniques such as phosphoramidatei H-phosphonate chemistry, or methylphosphoramidate chemistry (see, e.g., Uhlmann et al. (1990) *Chem. Rev.* 90:543–584; Agrawal et al. (1987) *Tetrahedron. Lett.* 28: (31):3539–3542); Caruthers et al. (1987) *Meth. Enzmol.* 154:287–313; U.S. Pat. No, 5,149,798). Oligomeric phosphorothioate analogs can be prepared using methods well known in the field such as methoxyphosphoramidite (see, e.g., Agrawal et al. (1988) *Proc. Natl. Acad. Sci. (USA)* 85:7079–7083) or H-phosphonate (see, e.g., Froehler (1986) *Tetrahedron Lett.* 27:5575–5578) chemistry. The synthetic methods described in Bergot et al. (*J. Chromatog.* (1992) 559:35–42) can also be used.

A specialized form of synthetic oligonucleotide called a hammerhead ribozyme can also be used to inhibit the expression of the CAPL gene. Ribozymes are RNA molecules which function both as antisense oligonucleotides hybridizing to the substrate and as catalytic molecules with the ability to cleave at specific phosphodiester linkages in RNA molecules to which they have hybridized, such as mRNAs, RNA-containing substrates, and Ribozymes, themselves.

Ribozymes can be prepared by the art-recognized methods such as phosphoramidate or H-phosphonate chemistry which can be carried out manually or by an automated synthesizer using standard H-phosphonate chemistry as described in U.S. Pat. No. 5,149,789, or using standard phosphoramidite chemistry (see, e.g., Beaucage (*Meth. Mol. Biol.* (1993) 20:33–61); Damha et al. (in *Protocols for Oligonucleotides and Analogs; Synthesis and Properties* (Agrawal, ed.) (1993) Humana Press, Totowa, N.J., pp. 81–114); or Uhlmann et al. (*Chem. Rev.* (1990) 90:534–583).

The flanking regions and other regions of the ribozyme may also be modified in a number of ways for protection against nuclease digestion, without compromising the ability of the ribozyme analog to hybridize to substrate RNAs. These modifications are essentially the same as those described above for synthetic oligonucleotides.

Alternatively, a representative CAPL-specific ribozyme DNA can be synthesized from two partially overlapping oligonucleotide primers containing respectively SalI and HindIII restriction sites. These are allowed to anneal to create a hemiduplex before PCR amplifications are performed. The PCR product consisting of a 48 bp ribozyme DNA flanked with the restriction sites can then be cloned into an expression vector such as pHβAPr-1 neo, which then can be transfected into and expressed by a mammalian cell line such as OHS.

Figure 3:
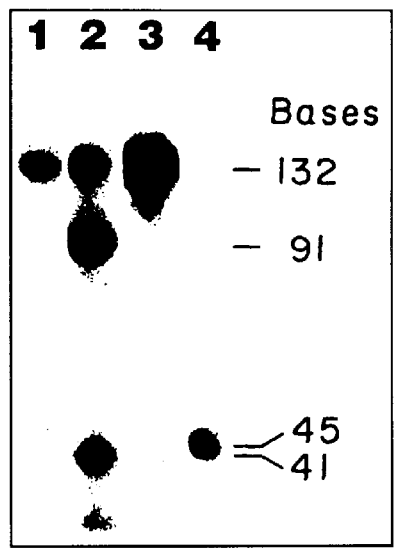
FIG. 3 is an autoradiogram of a denaturing polyacrylamide gel showing in vitro CAPL-inhibiting ribozyme activity, wherein lane 1 is $^{32}$P-CTP-labelled CAPL specific RNA; lane 2 is $^{32}$P-CTP-labelled CAPL-specific RNA mixed with unlabelled ribozyme; lane 3 is $^{32}$P-CTP-labelled CAPL-specific RNA mixed with unlabelled ribozyme. (no addition of $MgCl_2$) and lane 4 is $^{32}$P-CTP-labelled ribozyme-specific RNA.
Figure 2A:
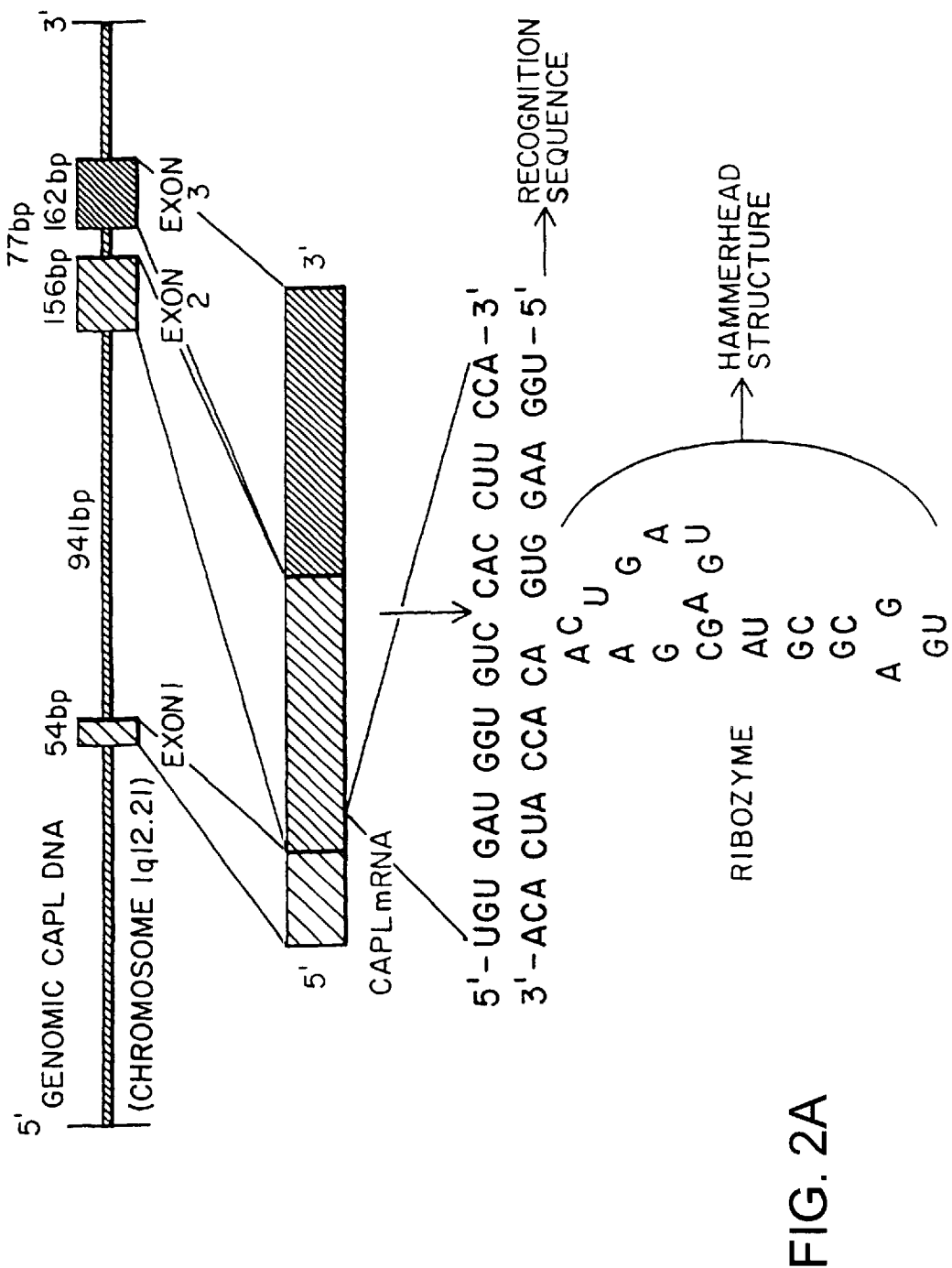
FIG. 2A is a schematic representation of the structure of the CAPL ribozyme with the conserved hammerhead sequence and the recognition sequences, and complementary CAPL mRNA (nt. 98–118) with a GUC cleavage site and the corresponding gene.

The structure of a representative hammerhead ribozyme, developed to specifically cleave the CAPL mRNA transcript after the GUC trinucleotide in codon 14, is shown in FIG. 2A. The in vitro activity of the ribozyme was examined by mixing in vitro transcribed ribozyme and $^{32}$P-labelled CAPL. Optimal cleavage conditions were found to be a molar ratio between substrate and ribozyme of approximately 1:1, incubated with 10 mM $MgCl_2$ at 37° C. for 1 hour. When the cleavage products were analyzed by denaturing polyacrylamide gel electrophoresis, it was demonstrated that the ribozyme had cleaved the 132 base target RNA into products of 91 and 41 bases, respectively (FIG. 3).

That CAPL plays a role in the development of metastatic cancer has been demonstrated both in vitro using a human metastatic cancer cell line and in vivo using two mammalian animal models of osteosarcoma.

The in vitro system was prepared from the metastatic human osteosarcoma cell line OHS (Fodstad (1986) *Int. J. Cancer* 38:33–40) which had been transfected with the mammalian expression vector pHβAPr-1 neo. This vector is under control of the constitutive human β-actin promoter (FIG. 2B), and contains a DNA encoding ribozyme specific for CAPL nucleic acid.

Figure 2B:
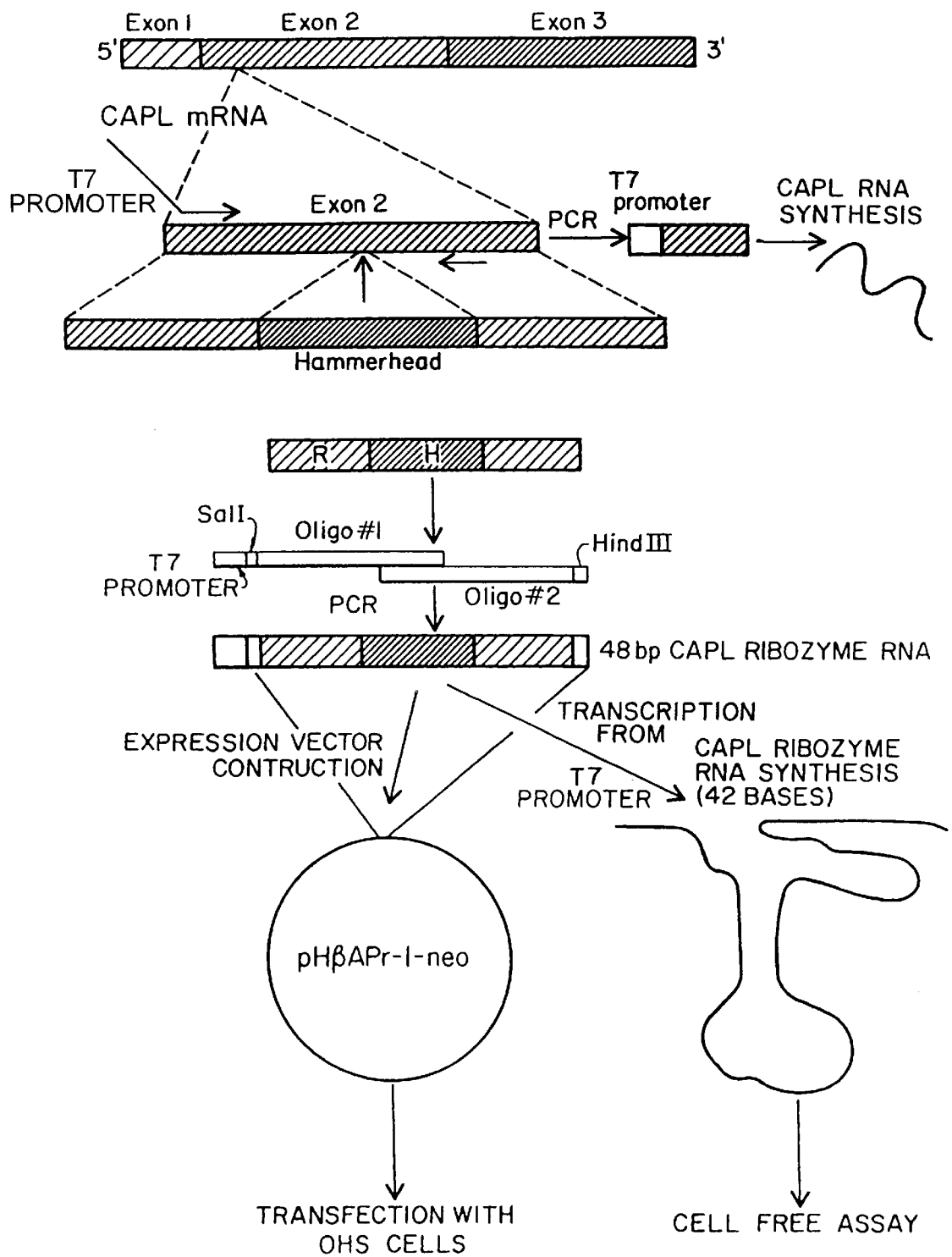
FIG. 2B is a diagram of the process of cloning the CAPL-specific ribozyme and of synthesizing the ribozyme- and target-specific RNAs.
Figure 4:
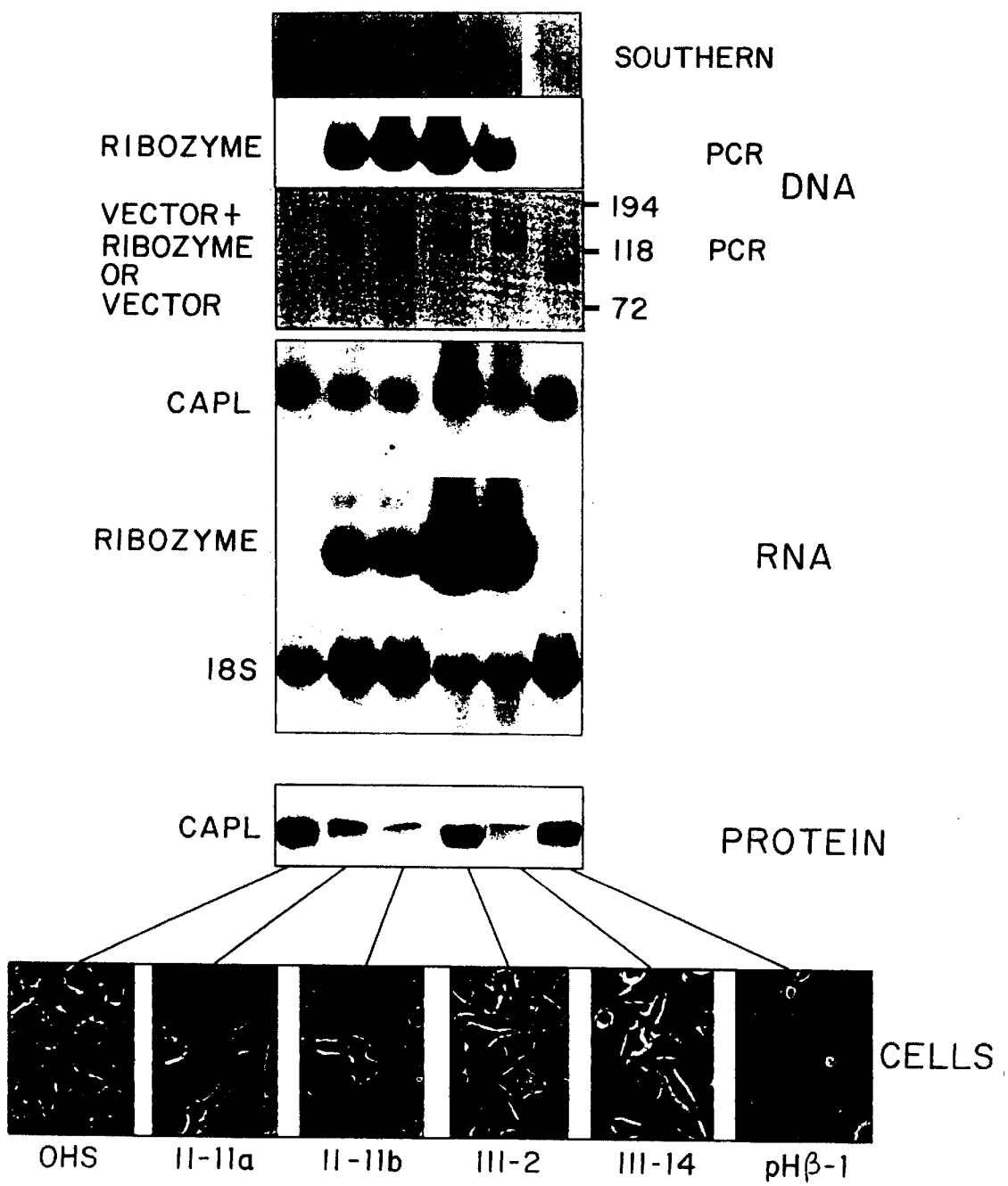
FIG. 4 is a diagram characterizing the CAPL specific ribozyme transfected into OHS cells clones II-11a, II-11b, III-2 and III-14, compared to both untransfected parental OHS cells and "vector-only" transfected cells, pHβ-1. Morphological pictures of all the cell clones, Northern blot analysts (with CAPL cDNA, CAPL ribozyme and 18S rRNA, for hybridization), Southern blot analysis (using CAPL ribozyme, detection of pIIβAPr-1-neo vector or ribozyme insert by RT-PCR analysis for hybridization), and Western blot analysis (stained with monoclonal antibody against CAPL) are shown.

Suppression of CAPL mRNA expression in ribozyme-transfected OHS cells was examined to determine the specificity of the ribozyme construct. The ribozyme was cloned into the mammalian expression vector pHβAPr-1 neo, which is under control of the constitutive human β-actin promoter (FIG. 2B). Both the vector, alone, and the cloned ribozyme construct were transfected into the metastatic human osteosarcoma cell line OHS (Fodstad et al. (1986) *Int. J. Cancer* 38:33–40). Individual geneticin-resistant colonies were picked, and 45 clone were grown and screened at the transcriptional level on Northern blots for both CAPL and ribozyme encoding mRNAs. The presence of ribozyme was found in 40 of the clones, as also confirmed by RT-PCR and Southern blot analysis. Ribozyme activity was considered present in a clone when the CAPL mRNA amount was 75% or less than the level in the parental and the vector alone transfected OHS cells. A marked reduction in CAPL transcript level was observed in 17 of the tested clones, all accompanied by moderate to high ribozyme expression. Moreover, Western blots prepared with anti-CAPL antibody revealed a close correlation between reduction in CAPL at the mRNA and protein levels (FIG. 4).

To screen for biological effects of the active CAPL ribozyme, three clones with significant reduction in CAPL mRNA and protein levels (FIG. 4) were selected for further characterization. One ribozyme-expressing clone without any observed reduction in CAPL levels (clone III-2) was included as control in addition to OHS parental and vector transfected cells. In addition to morphological effects, in vitro growth characteristics, and in vivo tumorigenicity and metastatic potential in nude mice and rats, were assessed.

When grown as monolayer, cultured OHS transformants with reduced CAPL expression showed altered morphology compared to the parental OHS cells. The parental cells exhibited a rounded cell shape, whereas the transformed cells tended to be more flattened and to spread more rapidly to cover the surface. Neither the proliferation rate of the transformed monolayer cells as compared to the parental cell line, nor the plating efficiencies in soft agar colony formation experiments were considerably altered.

To measure the adhesive properties of the cells, and their ability to grow as aggregates, the clones were cultivated as three dimensional aggregates (spheroids). The spheroids derived from the cells with reduced CAPL expression grew more slowly and demonstrated a decreased tendency to stick together when compared to the control spheroids, suggesting that the CAPL protein may influence some cell-cell adhesion properties.

In addition, in those clones expressing significant amounts of the CAPL-specific ribozyme and concomitantly reduced levels of CAPL RNA and protein, a dramatically lowered incidence of metastasis was observed in rats. Specifically, 90% metastasis was observed in cells expressing normal levels of CAPL RNA and protein versus 22% metastasis observed in cells expressing reduced levels of CAPL RNA and protein. This demonstrates the involvement of CAPL gene express in conferring the metastatic phenotype and that specific reduction in the expression of this gene can reduce metastatic potential of tumor cells.

Figure 6A:
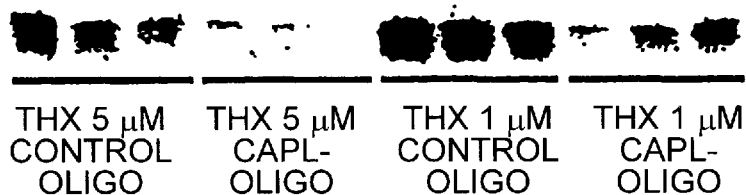
FIG. 6A is a representation of an autoradiogram of an SDS-polyacrylamide gel showing the inhibition of CAPL expression in human melanoma cells in vitro after treatment with control oligonucleotide or CAPL-specific oligonucleotide (SEQ ID NO:9)
Figure 6B:
FIG. 6B is a representation of an autoradiogram of an SDS-polyacrylamide gel showing the inhibition of CAPL expression in human sarcoma cells in vitro after treatment with control oligonucleotide or CAPL-specific oligonucleotide (SEQ ID NO:9).

Suppression of CAPL mRNA and protein in human osteosarcoma (KPDX) and melanoma (THX) cell lines was also demonstrated after treatment with CAPL-specific oligonucleotides directed to the 5' splice site (SEQ ID NO:5), the start codon (SEQ ID NO:22), the 3' end of the splice site before ATG (SEQ ID NO:23), and the ribozyme site (SEQ ID NO:9). The results are shown in FIGS. 6A and 6B and in Table 2.

TABLE 2

| Cell line | Treatment | Duration of Treatment | Oligo SEQ ID NO: | Results (frac. of antisense control) | Test |
|---|---|---|---|---|---|
| OHS | 5 μM oligo | 7 days | 5 | 0.90 | Protein |
| | | | 23 | 0.98 | Protein |
| | | | 5 + 23 | 0.92 | Protein |
| | | | 9 | 0.88 | Protein |
| | 5 μM oligo with Lipofectin | 7 days | 23 + 9 | 0.84 | Protein |
| | | | 9 | 0.90 | Protein |
| KPDX | 5 μM oligo | 10 days | 5 | 1.13 | RNA |
| | | | 22 | 1.12 | RNA |
| | | | 23 | 1.26 | RNA |
| | | | 5 + 23 | 0.88 | RNA |
| | | | 9 | 0.84 | RNA |
| KPDX | 5 μM oligo with DOTAP | 10 days | 5 | 0.87 | RNA |
| | | | 22 | 0.81 | RNA |
| | | | 23 | 0.76 | RNA |
| | | | 5 + 22 | 0.73 | RNA |
| | | | 9 | 0.73 | RNA |
| KPDX | 5 μM oligo with DOTAP | 12 days | 9 | 0.30 | Protein |

Human metastatic tumor models have been established in nude mice (see, e.g., Kjonniksen et al. (1994) Cancer Res. 54:1715–1719) and in nude rats (see, e.g., Weterman et al. Cancer Res. 52:1291–1296) by direct inoculation of human cancer cells. Using these and similar models, a correlation has been determined between the expression of the CAPL gene and the progression of metastatic cancer.

More particularly, clones prepared from human osteosarcoma cells transfected with a CAPL-specific ribozyme were examined by subcutaneous implantation into nude mice. Importantly, no clear differences between the parental cell line and the ribozyme transformants in tumor take, lag time, or proliferation rate were observed. These results are in agreement with the in vivo growth characteristic, and suggest that the proliferation potential per se was not affected by ribozyme activity.

The ability of synthetic oligonucleotides to suppress the metastatic phenotype in immunodeficient rats treated with intracardial tumor cell injection (Kjonniksen et al. (1994) Cancer Res. 54:1715–1719; Kjonniksen et al. (1990) J. Nat. Cancer Inst. 82(5) March) was also studied. In this nude rat model system, the metastatic potential of the parental cells and OHS clones with reduced CAPL expression was compared. In animals injected with parental OHS cells, 33 of 37 rats (89%) developed bone metastases, whereas only two of 15 (13%), four of 16 (25%) and four of 15 (27%) rats injected with the ribozyme expressing cell clones II-11, II-11B and III-14, respectively, developed metastatic disease. With vector-transfected control cells bone marrow metastases developed in 11 of altogether 14 rats (78%). The marked difference between clones with ribozyme-induced reduction in CAPL expression and the control cells was further demonstrated by the delay in metastasis development in rats injected with ribozyme-expressing cells. Thus, the average lag times before symptom-giving metastasis developed were more than 50 days for all the ribozyme-transfected clones, compared to only 28 days for OHS cells and 29 days for the "vector-only" transfected cells., Importantly, all the ribozyme-expressing cell clones showed a marked reduction in CAPL mRNA and protein levels as compared to OHS (FIG. 4). In contrast, the ribozyme-transfected clone III-2 without reduction in CAPL mRNA or protein levels had retained the metastatic potential of the parent OHS cells. These data further strengthen the evidence for a close relationship between CAPL expression and metastatic capacity of the osteosarcoma cells.

In another experiment, tumor cells in the bone marrow of nude rats injected with OHS cells and the various clones were isolated by immunomagnetic beads coated with anti-human antibodies, and subsequently analyzed by RT-PCR for expression of both CAPL and ribozyme-encoding mRNAs. Ribozyme-specific PCR products were observed (FIG. 3), indicating that the ribozyme designed was in fact active and site specific- In conclusion, modulation of the CAPL gene expression by a CAPL-specific oligonucleotide reverses the metastatic phenotype of the human osteosarcoma cell line OHS. This is the first demonstration of one sole gene product being able to cause a total change in metastatic behavior of human tumor cells by an in vivo assay.

The synthetic antisense oligonucleotides of the invention in the form of a therapeutic formulation are useful in treating or inhibiting metastatic cancer such as osteosarcoma, breast cancer, etc. They may be used as part of a pharmaceutical composition when combined with a physiologically and/or pharmaceutically acceptable carrier. The characteristics of the carrier will depend on the route of administration. Such a composition may contain, in addition to the synthetic oligonucleotide and carrier, diluents, fillers, salts, buffers, stabilizers, solubilizers, and other materials well known in the art. The pharmaceutical composition of the invention may also contain other active factors and/or agents which enhance inhibition of CAPL expression. For example, combinations of synthetic oligonucleotides, each of which is directed to different regions of the CAPL mRNA, may be used in the pharmaceutical compositions of the invention. The pharmaceutical composition of the invention may further contain other chemotherapeutic drugs. Such additional factors and/or agents may be included in the pharmaceutical composition to produce a synergistic effect with the synthetic oligonucleotide of the invention, or to minimize side-effects caused by the synthetic oligonucleotide of the invention. Conversely, the synthetic oligonucleotide of the invention may be included in formulations of a particular anti-CAPL or anti-metastatic cancer factor and/or agent to minimize side effects of the anti-CAPL factor and/or agent.

The pharmaceutical composition of the invention may be in the form of a liposome in which the synthetic oligonucleotides of the invention is combined, in addition to other pharmaceutically acceptable carriers, with amphipathic agents such as lipids which exist in aggregated form as micelles, insoluble monolayers, liquid crystals, or lamellar layers which are in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323. The pharmaceutical composition of the invention may further include compounds such as cyclodextrins and the like which enhance delivery of oligonucleotides into cells, or such as slow release polymers.

As used herein, the term "therapeutically effective amount" means the total amount of each active component of the pharmaceutical composition or method that is sufficient to show a meaningful patient benefit, i.e., reduction in metastatic tumors. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of one or more of the synthetic oligonucleotide of the invention is administered to a subject afflicted with metastatic or premetastatic cancer. The synthetic oligonucleotide of the invention may be administered in accordance with the method of the invention either alone of in combination with other known therapies for metastatic cancer. When co-administered with one or more other therapies, the synthetic oligonucleotide of the invention may be administered either simultaneously with the other treatment(s), or sequentially. If administered sequentially, the attending physician will decide on the appropriate sequence of administering the synthetic oligonucleotide of the invention in combination with the other therapy.

Administration of the synthetic oligonucleotide of the invention used in the pharmaceutical composition or to practice the method of the present invention can be carried out in a variety of conventional ways, such as intraocular, oral ingestion, inhalation, or cutaneous, subcutaneous, intramuscular, or intravenous injection.

When a therapeutically effective amount of synthetic oligonucleotide of the invention is administered orally, the synthetic oligonucleotide will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% synthetic oligonucleotide and preferably from about 25 to 90% synthetic oligonucleotide. When administered in liquid form, a liquid carrier such as water, petroleum, oils of animal or plant origin such as peanut oil, mineral oil, soybean oil, sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the synthetic oligonucleotide and preferably from about 1 to 50% synthetic oligonucleotide.

When a therapeutically effective amount of synthetic oligonucleotide of the invention is administered by intravenous, cutaneous or subcutaneous injection, the synthetic oligonucleotide will be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the synthetic oligonucleotide, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of synthetic oligonucleotide in the pharmaceutical composition of the present invention will depend upon the nature and severity of the condition being treated, and on the nature of prior treatments which the patent has undergone. Ultimately, the attending physician will decide the amount of synthetic oligonucleotide with which to treat each individual patient. Initially, the attending physician will administer low doses of the synthetic oligonucleotide and observe the patient's response. Larger doses of synthetic oligonucleotide may be administered until the optimal therapeutic effect is obtained for the patient, and at that point the dosage is not increased further. It is contemplated that the various pharmaceutical compositions used to practice the method of the present invention should contain about 1.0 ng to about 2.5 mg of synthetic oligonucleotide per kg body weight.

The duration of intravenous therapy using the pharmaceutical composition of the present invention will vary, depending on the severity of the disease being treated and the condition and potential idiosyncratic response of each individual patient. It is contemplated that the duration of each application of the synthetic oligonucleotide will be in the range of 12 to 24 hours of continuous intravenous administration. Ultimately the attending physician will decide on the appropriate duration of intravenous therapy using the pharmaceutical composition of the present invention.

The following examples illustrate the preferred modes of making and practicing the present invention, but are not meant to limit the scope of the invention since alternative methods may be utilized to obtain similar results.

EXAMPLES

1. Determination of CAPL Oligonucleotide Sequences

To determine the optimal sequence for antisense inhibition of CAPL expression, RNase H analysis of the CAPL mRNA was performed as described by Frank et al. (*Proc. Int. Conf. Nucleic Acid Med. Applns.* (1993) 1:4.14 (abstract)). Briefly, CAPL mRNA was incubated with a library of random oligonucleotides and a limiting amount of RNase H followed by analysis of the mRNA by gel electrophoresis to identify RNase H sensitive sites. At least five 20mer phosphorothioate oligonucleotides are synthesized to target each RNase H site: one which directly spans the site and four which are staggered by three bases 5' and 3' to the initial oligonucleotide. Representative oligonucleotides discovered by this analysis have SEQ ID NOS:3–10.

2. Preparation of Oligonucleotides

Unmodified (PO) and modified (PS) oligonucleotides were synthesized on an automated synthesizer (Millipore 8700, Millipore Corp., Bedford, Mass.) using phosphoramidate chemistry (see Agrawal et al. (1989) *Proc. Natl. Acad. Sci.* (U.S.A.) 86:7790–7794; McBride et al. (1983) *Tetrahedron Lett.* 24:245). The oxidation reagents used in the syntheses were standard solution of iodine, for phosphodiester linkages, and $^3$H-1,2-benzodithiole-3-one-1,1-dioxide as a solution of 1 g in 100 ml of acetonitrile, for phosphorothioate linkages formation. Methylphosphonates were prepared according to the method of Beaucage, "Oligonucleotide Synthesis: Phosphoramidite Approach" in *Protocols for Oligonucleotides and Analogs, Methods in Molecular Biology* (1994) 20:33–62). Oligonucleotide concentrations were determined by absorbance at 260 nm, taking into account the molar extinction coefficient of the nucleotides present in each sequence (Ausubel et al. (eds.) (1987) *Current Protocols in Molecular Biology* (Wiley, New York))

3. Preparation of Ribozyme, Probes, and Antibodies

To provide a ribozyme specific probe, primers used for cloning the ribozyme described above (SEQ ID NOS:11 and 12) were kinased, annealed and ligated. The ligation mix was subsequently labelled with $^{32}$P-dCTP as described by Maelandsmo et al. (*British J. Cancer* (1995) in press) An oligonucleotide probe specific for human 18S ribosomal RNA, and complementary to nucleotides 287 to 305 was used for calibrating the Northern blots. For Western blot analysis, supernatant from a hybridoma culture containing monoclonal antibody directed against human CAPL was used.

Oligonucleotides CAPL-rib-1 and CAPL-rib-2 (having SEQ ID NOS:11 and 12, respectively), were constructed for cloning of the CAPL ribozyme (with flanking SatI and HindIII sites). Oligonucleotide primers T7-rib-1 and rib-2 (having SEQ ID NOS:13 and 14, respectively) were constructed for the synthesis of a CAPL-specific ribozyme (with the T7 RNA polymerase promoter). Oligonucleotide primers T7-CAPL-ex-1 and CAPL-ex-2 (having SEQ ID NOS:15 and 16, respectively) were constructed for the synthesis of CAPL substrate (with the T7 RNA polymerase promoter). PCR-primers pHb-1 and pHb-2 (having SEQ ID NOS:17 and 18, respectively) were constructed for detecting CAPL-ribozyme expression in the transfected cells. A probe (having SEQ ID NO:19) for the CAPL-specific which is complementary to conserved catalytic sequence of the ribozyme was also constructed. PCR-primers CAPL-ex-1 and CAPL-ex-2 (having SEQ ID NOS:20 and 21, respectively) were constructed for detecting CAPL mRNA.

These primers and probes were prepared by standard methods using reverse transcriptase (see, e.g., Weterman et al. (1992) *Cancer Res.* 52:1291–1296).

A hammerhead ribozyme was constructed according to the protocol described by Kashani-Sabet et al. (*Antisense Res. Dev.* (1992) 2:3–15). The GUC trinucleotide in codon 14 in CAPL mRNA was selected as the ribozyme cleavage site (FIG. 2A). Two partially complementary oligonucleotide primers (SEQ ID NOS:11 and 12) encoding the catalytic core of the hammerhead ribozyme were mixed and allowed to form a hemiduplex. In addition, the primers were complementary to 11 or nine nucleotides on each side of the cleavage site in CAPL mRNA and contained flanking SalI and HindIII restriction sites (primer SEQ ID NOS:7 and 8). PCR amplification resulted in a 52-bp ribozyme DNA that subsequently was ligated into the mammalian expression vector pHβApr-1 neo (pHβ) (Gunning et al. (1987) *Proc. Natl. Acad. Sci.* 84:4831–4835). The sequence and orientation of the insert was confirmed by sequencing using the Sequenase kit, Version 2.0 (U.S. Biochemical Corp., Cleveland, Ohio).

4. In vitro Transcription of RNA from Synthetic DNA Templates

Templates for in vitro transcription of both ribozyme and target RNAs were generated by PCR. The PCR products were amplified from the vector pHβApr-1 neo with ribozyme insert or from total RNA isolated from OHS cells, using primers with SEQ ID NOS:9 and 10. Subsequently, in vitro transcriptions were performed by mixing 0.5 μg PCR-product (DNA-template) with 20 u T7-RNA polymerase as described by Sambrook et al. (*Molecular Cloning, a Laboratory Manual* (2d ed.) Cold Spring Harbor Laboratory Press, (1989) New York, pp. 5.58 and 17.11–17.16). For radioactive labelling of the transcripts 60 μCi $^{32}$P-CTP (800 Ci mmol$^{-1}$, Amersham, UK) were added. After DNAse digestion of the templates, the mixtures were extracted once with phenol before purification on a NENSORB 20 cartridge (Du Pont, NEN Products, Hartfordshire, UK) according to the manufacturer's manual.

5. In vitro Ribozyme Cleavage Reaction

The cleavage reaction was carried out as described by Kashani-Sabet et al. (Antisense Res. and Dev.) by mixing equal molar ratios of in vitro transcribed $^{32}$P-labelled CAPL substrate and CAPL specific ribozyme. The cleavage reaction was initiated by adding 10 mM MgCl$_2$. After incubation for 1 h at 37° C., the cleavage reaction products were analyzed by denaturing polyacrylamide gel electrophoresis.

6. In vitro Studies

A. Cells

The OHS cell line was established from a bone tumor biopsy obtained from a patient with multiple skeletal metastasis and grown as monolayer cultures in RPMI medium containing 10% fetal calf serum as described by Fodstad et al. (*Int. J. Cancer* (1986) 38:33–40). Growth curves of the tumor cells were constructed and the cell doubling time was measured from the exponential part of the curves. Cultivation in soft agar was performed (Tveit (1981) *Int. J. Cancer* 28:3229–334) and the plating efficiency (PE) was defined as the number of colonies formed in percentage of the number viable cells plated. Spheroid formation and growth were obtained as by Fodstad et al. (1986) ibid.)) . The diameter of the spheroids was measured three times weekly by means of an ocular micrometer, and the relative volumes were calculated (Wibe (1984) *Int. J. Cancer* 34:21–26).

The KPDX cell line was established from a patient with a primary osteosarcoma, and grown as a monolayer culture in RPMI growth medium containing 10% fetal calf serum. The KPDX cell line shows a high expression of the CAPL mRNA and protein, as analyzed using Northern blot and immunoblotting techniques, respectively.

The THX cell line was isolated from a patient carrying a lymph node with metastatic deposits of amelanotic melanoma cells. The cell line was kept as a monolayer culture grown in RPMI supplemented with 10% fetal calf serum. The cell line shows a low to moderate expression of the CAPL protein as visualized using SDS-PAGE protein electrophoresis, blotting and immunostaining.

Figure 5:
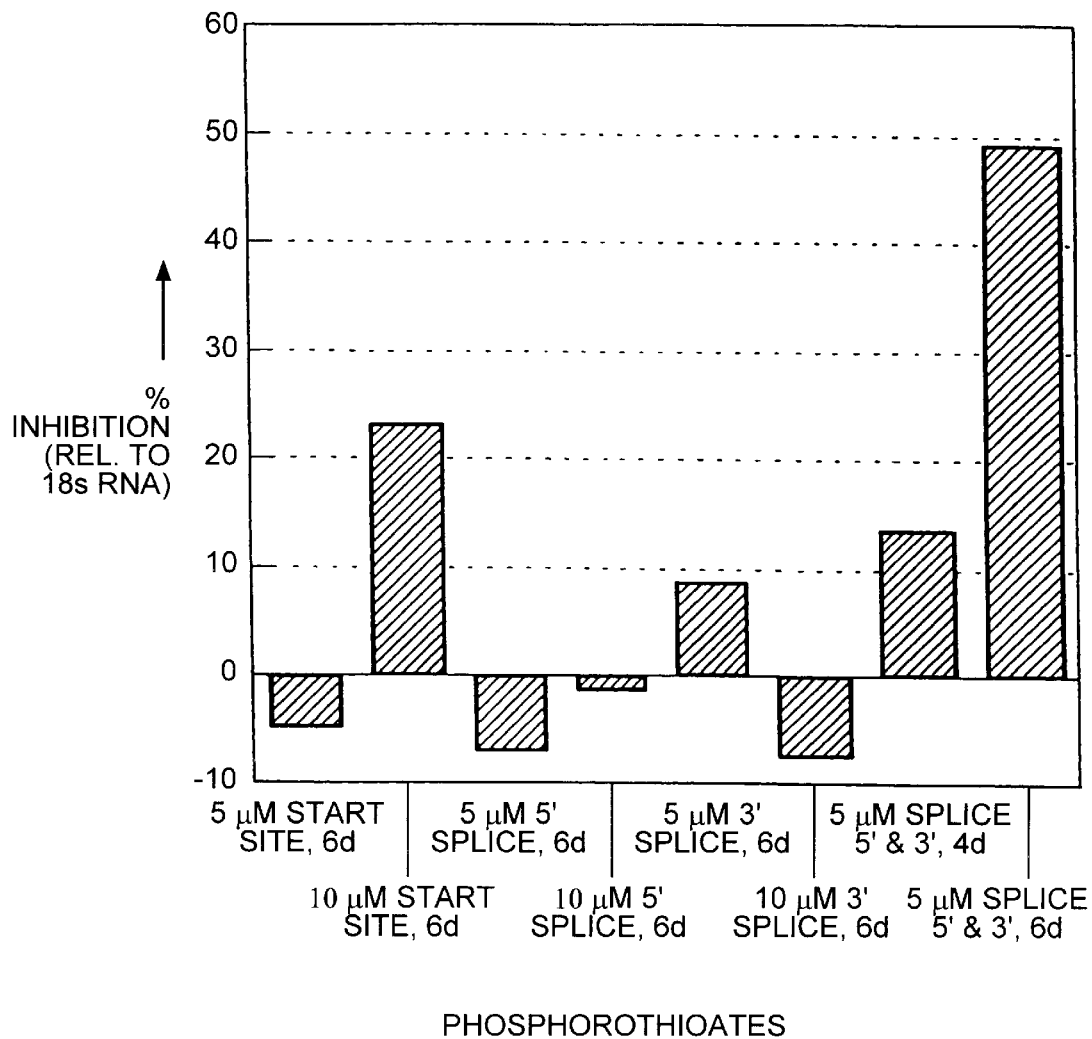
FIG. 5 is a graphic representation of the inhibition of the expression of CAPL mRNA in human osteosarcoma cells treated with CAPL-specific oligonucleotides of the invention.

B. Activity of Oligonucleotides 0.5, 2, 5 and 10 μM of synthetic oligonucleotide having SEQ ID NOS:3,5,7, and 9 were used to assess antisense activity in the OHS cell. Specifically, 2×10$^5$ cells were seeded into a small cultivation flask (25 cm$^2$) and the indicated amount of oligonucleotide added the next day. This was done in the presence and absence of 2.5 or 5 µg/ml lipofectin (Gibco/BRL/LifeTechnologies, Denmark). When lipofectin was used the cells were treated in serum-free medium for 4 hours, after which sufficient serum is added to make the medium 10%. 20 hours later, the cells were media changed and fresh oligonucleotide is added. The cells were then treated in an identical fashion as were those cells which do not receive lipofectin. On the third day after seeding, the cells were media changed and fresh oligonucleotide added. The cells were analyzed on the sixth day after seeding for mRNA level in relation to control (non-antisense) oligonucleotide by standard procedures (see, e.g., Sambrook et al. (1989) *Molecular Cloning, a Laboratory Manual*, Cold Spring Harbor Press, New York). Some representative results are shown in FIG. 5, which demonstrate the ability of CAPL-specific oligonucleotides, alone or in combination, to inhibit the transcription of CAPL mRNA. The CAPL protein is also determined in parallel cultures via Western blot using CAPL monoclonal antibody according to standard procedures.

The activity of the oligonucleotides (SEQ ID NO:5 (splice site), SEQ ID NO:22 (including start codon), SEQ ID NO:23 (3' end of splice site before ATG), and SEQ ID NO:9 (ribozyme site)) was tested in the KPDX and THX cell lines using a concentration of 1 µM and 5 µM, during the 12 day incubation period. Lipofectin or the DOTAP transfection agent (Boelaringer Mannheim GmBh, Germany) was used in these experiments at the concentration and by the procedure recommended by the manufacturer. Cells were seeded at low density ($2 \times 10^3$ cells/dish) into individual 3 cm diameter cell culture dishes, in a total volume of 3 ml RPMI supplemented with 10% fetal calf serum. The following day the suspension containing the oligonucleotide was boiled for 5 minutes, diluted in RPMI without fetal calf serum, and mixed with an equal volume of RPMI containing the DOTAP transfection agent. The mixture was then left to incubate at room temperature for 10 minutes before the addition to the culture medium (RPMI containing 10% fetal calf serum) in the dish. The culture medium was renewed after 4 and 8 days and new antisense oligonucleotide was added as described above. The cells were then harvested and analyzed for CAPL expression using SDS-PAGE protein electrophoresis, blotting onto Immobilon membrane (Millipore AB/Enebakkveien, Norway), and a CAPL-specific monoclonal antibody (produced according to a variation of the protocol of Kriajevska et al. (*J. Biolog. Chem.* (1994) 269:19679–19682) in a standard immunostaining protocol. The CAPL protein expression in the treated cells were compared with cells treated with control oligonucleotide (scrambled version of SEQ ID NO:9). The results are shown in FIGS. 6A and 6B.

C. Activity of Ribozyme $4 \times 10^5$ OHS cells were resuspended in 5 ml Dulbecco's modified Eagle's medium and seeded out in 25 cm² culture flasks. The cells were allowed to grow overnight before transfection with 5 µg or 10 µg ribozyme containing plasmid in accordance with the calcium phosphate precipitation method described by Chen et al. (*Mol. Cell. Biol.* (1987) 7:2745–2752. Transfection with the plasmid pHβApr-1 neo, without the ribozyme sequence, served as a negative control. Transfected cells with integrated plasmid were selected for in RPMI growth medium containing 400 µg/ml geneticin (G418 disulfate, GIBCO) for 6–8 weeks. Individual G418-resistant colonies were picked, grown, and screened for expression of both CAPL and ribozyme by PCR and Northern blot analysis as described below. The cells were added G418 some weeks later to test for the presence of the neomycin gene.

7. In vivo Assays

Congenitally athymic Balb/C rnu/rnu mice and Rowett Han:rnu/rnu rats were used in this study. Single OHS cell suspensions were obtained from subconfluent monolayer cultures. $1 \times 10^6$ cells were injected subcutaneously (s.c.) into the flanks of nude mice, or intracardially into the left ventricle (l.v.) of immunodeficient rats as described by Kjonniksen (*J. Natl. Cancer Inst.* (1990) 82:408–412). The volume of the s.c. growing tumors was calculated according to the formula 0.5*length*width2 (Fodstad (1980) *Br. J. Cancer*, 41 (Supple. IV):146–149). Upon l.v. injections, the animals were followed by daily inspections and sacrificed at the first sign of paresis or walking impairment reflecting metastatic disease in the spine.

8. Northern Blot Analysis

Total cellular RNA was prepared by the guanidinium thiocyanate-cesium chloride method described by Sambrook et al. (*Molecular Cloning, a Laboratory Manual* (2d ed.) Cold Spring Harbor Laboratory Press (1989), New York, pp. 7.5, 7.19–7.22. Samples of 5 µg total RNA were separated by 1% agarose-formaldehyde gel electrophoresis and blotted onto Hybond-N+ membranes (Amersham, Arlington Heights, Ill.) according to the manufacturer's manual. After baking for 2 hours and subsequent ultraviolet crosslinking, the filters were hybridized with $^{32}$P-labelled DNA probes, encoding CAPL or the CAPL specific ribozyme as described by Maelandsmo (*British J. Cancer* (1995) in press). For multiple hybridizations, the bound probe was removed by incubating the filters twice for 5 min in 0.1×SSC and 0.1% SDS at 95°–100° C. To correct for uneven amounts of RNA loaded in each lane, the filters were rehybridized with a kinase labelled oligonucleotide probe (19mer) specific for human 18S rRNA. The levels of specific mRNAs were adjusted relative to the amount of 18S rRNA after scanning of the autoradiograms in a computing Densitometer (Molecular Dynamics, Sunneyvale, Calif.).

Alternatively, RT-PCR was used to screen for CAPL or ribozyme specific RNA in the transfected cells. Total RNA (200 ng) isolated from the different cell clones were reverse transcribed by 5 u MMLV-reverse transcriptase (Superscript II, GIBCO/BRL/LifeTechnologies, Denmark) and PCR using primers having SEQ ID NOS:13 and 14 having SEQ ID NOS:16 and 17 were performed. After amplification and separation on PAGE, the ribozyme specific PCR-products were blotted onto Hybond-N+ membranes (Amersham, Arlington Heights, Ill.) and hybridized with a kinase labelled (Sambrook et al. (1989) *Molecular Cloning, a Laboratory Manual* (2ed) Cold Spring Harbor Laboratory Press, New York, pp. 5.68–5.72) oligonucleotide probe encoding the hammerhead sequence.

9. Southern Blot Analysis

Genomic DNA was isolated by standard methods (see, e.g., (Sambrook et al. (1989) *Molecular Cloning, a Laboratory Manual* (2d ed.) Cold Spring Harbor Laboratory Press, New York, pp. 6.53). Aliquots (8 µg) of DNA were digested with HindIII, separated on 0.8% agarose gels and transferred by alkaline blotting onto Hybond-N+ membranes (Amersham, Arlington Heights, Ill.), according to the manufacturer's manual. The membranes were prepared, hybridized and washed as previously described. For multiple hybridizations, the bound probe was removed by incubating the filters for 15 min at room temperature in 100 mM sodium hydroxide and 1 mM EDTA.

10. Western Blotting

Protein lysates from the cells were made according to standard methods (see, e.g., Sambrook et al. (1989) *Molecu-* lar Cloning, a Laboratory Manual (2d ed.) Cold Spring Harbor Laboratory Press, New York, pp. 18.62–18.63) and separated by 15% SDS-polyacrylamide gel electrophoresis (see, e.g., Sambrook et al. (1989) *Molecular Cloning, a Laboratory Manual* (2d ed.) Cold Spring Harbor Laboratory Press, New York, pp. 18.47–18.48). After transfer onto an Immobilon-P membrane (Millipore Corporation, Bedford, Mass.) according to the manufacturer's manual, the membranes were blocked by PBS containing 5% dry milk and 5% fetal calf serum. Subsequently, the membranes were incubated with hybridoma culture medium supernatant containing monoclonal antibody directed against CAPL, washed and incubated with blocking solution containing a 1:2000 dilution of horseradish peroxidase-conjugated rabbit anti-mouse antibody (Dako, Glostrup, Denmark). The immunoreactive proteins were visualized using the ECL Western blotting detection system (Amersham, UK).

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed is:

1. A synthetic oligonucleotide which inhibits expression of mRNA encoding CAPL, which oligonucleotide has a sequence that is complementary to a sequence of said CAPL MRNA that includes the 3' splice site in the portion of said CAPL nRNA which is complementary to SEQ ID NO:3.

2. The synthetic oligonucleotide of claim 1, said oligonucleotide having the nucleotide sequence shown as SEQ ID NO:3 or 4.

3. A synthetic oligonucleotide which inhibits expression of mRNA encoding CAPL, which oligonucleotide has a sequence that is complementary to a sequence of said CAPL mRNA that includes the 5' splice site in the portion of said CAPL mRNA which is complementary to SEQ ID NO:5.

4. The synthetic oligonucleotide of claim 3, said oligonucleotide having the nucleotide sequence shown as SEQ ID NO:5 or 6.

5. A synthetic oligonucleotide which inhibits expression of nRNA encoding CAPL, which oligonucleotide has a sequence that is complementary to a sequence of said CAPL MRNA that includes the translational start site in the portion of said CAPL DRNA which is complementary to SEQ ID NO:7.

6. The synthetic oligonucleotide of claim 5, said oligonucleotide having the nucleotide sequence shown as SEQ ID NO:7, 8, or 22.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 10952 base pairs
        ( B ) TYPE: nucleic acid
        ( C ) STRANDEDNESS: single
        ( D ) TOPOLOGY: linear ( i i ) MOLECULE TYPE: genomic DNA ( i i i ) HYPOTHETICAL: NO ( i v ) ANTI-SENSE: NO ( x i ) SEQUENCE DESCRIPTION: SEQ ID NO:1:

```
GAGCTCCAGC  CACTGGCCAG  CCTTCATGTG  ACTCTAGCCC  AAATTCATTC  CCATCACCTG       60
GGGTGGAAGG  GCCAGAAATC  TCAAGCTTAG  ACTCTGGAAG  TGCCCCTGGG  AGGAACACAC      120
CTCCTTCCTG  TGCCTCAAAG  ACATCCCACC  TGATGATTTC  CCCCTGGGAA  GCAAGCAGTT      180
CACAGCCAAA  AGCTGGGATC  TGGTCAGGCA  AGTTCAGACT  TCTCGTCTGT  AAAGGGGAGG      240
CTTAGCCACG  TGCTCTCCAA  GTTCTACCCG  GAATAGAGAT  TTGTAGGGGT  GCAACCTGAG      300
CGAGGCAGAA  GTGTGTCCCC  ACTTGGTATT  CTGGGGGCCT  CTGCAGAGTG  AAGAGATGGG      360
GCTGTGATGT  GATGGATAAG  CCAGACTGTC  TCCTCCAACT  GAGCTGGAAG  GACTTGGCAG      420
GAGACTGTCC  CCTGTTCCCA  ACTCTGGGGG  AGGGCAGATG  GGGAATGAAA  GGGGAGTGGT      480
GTCTGAGCCC  AGACTGGCCT  TTGATGTGTG  CGTGGATAGG  TGGGCAGGTG  GGGCCTGTAA      540
TGGGTCTGCT  GAGGGATCCC  TGAGGGCATC  CTCAGTGTTG  ACCTACTTGT  GTCCCCATA      600
ATTGCTTCCT  TCCTTTCTTG  GGAGGCTACA  AATAGTGACG  CCCTGTCTCT  AAGCTCCTAC      660
AGCTGAAACG  CCAGCACCAG  TGGTGAGTGC  CAGCTGCTTG  GGTCCTGCCC  TGGGTTGAGT      720
GTCAGGGCAG  TTTGGGGACC  CCCAGTAGCC  AGCCTGACTC  CTGACCCAGG  GTCTGGCATT      780
GGAAGCAGAG  AGATGACCAC  AGGCGGGCCT  GACACGGGGA  GGGAAGTCAG  ATATAGTGGA      840
CGCAGAGGTT  TCCTTACACA  GTGAGGGCT  GTTGGGGAAG  TTTGGGCAGG  GAGGTGTGTA      900
GAGCTAAGGT  CTGCCTTGGG  TGGAGCACTG  GGCTCAAGGC  TCTGGTCTTC  CCCTTGATCA      960
GGCCCCTCAC  CTGCTCCTTG  CCTCCTTGCT  TCACCTCTGA  GTCTCCTCAT  TTCTGAGGAT     1020
CATGGCCCTT  TCCTCTCCTG  GGAACCTGGA  CACCTTGCTC  TAATCCTGGG  GTGTTTACAA     1080
TGAATTAAAT  CCTGGCAGTG  CTTGGCACTC  CCCACTCCCC  TTCCCCTACT  TTCCTGCCAG     1140
CCACAACCAT  GCCAGCCATT  TGCTCCCAGC  AGGGGCCCA  GCAGTGGGCA  AATCTTCAGG     1200
```

| | | | | | |
|---|---|---|---|---|---|
| GAGAGTCTTG | GCCCTGGCCG | CCCTGTGCTG | CAGGACTCTT | GTCCCGTGGG | GGAATCAGGA | 1260
| GTGAGTCACT | GGGCTAGCAT | GGAAAAAATT | CTTGCCTTCC | TGGCTGCCTT | CGGGTTTTCC | 1320
| CAGGCTGGAG | GCATCATCCC | AGAAGGGCGG | TGGAAGGGGA | CAGTGGAAGT | GGGGGGAGGT | 1380
| GAGCAATTCC | AGGAAGGGCT | TCCCCTCCAA | TAGAACAGAG | TATCCCTATA | CAGAACCTCC | 1440
| CTGCTCAAAA | CCCCCAGGGG | TCGGGAGGGT | AACCTCAGGG | GAGGCCAGTC | TCAGATTGGT | 1500
| AAACACCCGA | ACTGGTCAAC | TCTCAAGAGA | CCATCTGGTT | CAGGTTCCTG | ACTGGGCCAG | 1560
| CGAGGTGAGA | TGAACCCCAA | CTTACAGATC | AGGCCCCGCC | CCTGAGACCC | AGAGAGACAA | 1620
| ATGGCTCACC | AAGGTTGCAC | AGCTGGCGAC | AGGCAGAGAG | GATCCCACAA | GTTTTTCTTC | 1680
| TGGGTGCAGC | TTCCTCGAGT | TCAGGGCAGG | AGGCAGGGTG | AGGGCAGTGG | TGGTGAGGCT | 1740
| GTGGGGGCGC | CTCTCAGACC | TGCCCCTCCC | TGCTAAGGCC | TAGCTTCTCC | AAGGGCTGAG | 1800
| GGCAGAGAAG | CACAGGGCCA | GGCTCTCCTT | GTGCAAGTTC | CTGCAGGGAG | GGAGGCTTCT | 1860
| AGGGCATCTC | ATGGGCTGGG | GCAGACTGGG | ACCGAGCCAT | CCCTGGTTGT | TGGGGATAAG | 1920
| AAGAGGTGGC | AGATAATCTG | AGAGTGCTTA | AGGAGCCCCA | CGGTGGGGTG | TGTGGGTGGT | 1980
| GGGGTAGGAT | GCTGTCTCTC | TGAGGAGTTT | ACAGCGATGT | TGGGGCAATG | AGACCTCTAC | 2040
| ATGGGGAAAT | AACAACAGGA | CAGCAGGGGG | ATAAATTAGG | AGGGCTGGTG | TGGTCTGGGA | 2100
| GGGCTACTCA | GAGGAGGGGG | AGACTGCGGG | GCCTGAAGCC | TGATGGAGGT | TAAGATGGGT | 2160
| CTGGGAACAG | TCTCTGAGAA | ACACAGAGGG | CAGAGGTGAG | CTGGGGGGCT | GGCCTGGAAC | 2220
| TCTGCTGTGA | GCCACACCCT | TGTTCTGTGA | CAGTGAGGAT | GGCCAGGCCT | CTGGAGCAGG | 2280
| CGGTAGCTGC | CATCGTGTGC | ACCTTCCAGG | AATACGCAGG | GCGCTGTGGG | GACAAATACA | 2340
| AGCTCTGCCA | GGCGGAGCTC | AAGGAGCTGC | TGCAGAAGGA | GCTGGCCACC | TGGACCCCGG | 2400
| TGAGCAGTCA | GAGTGTCCGT | CCCCTCCTCC | TCCGGGGGGA | GGCACTGCCT | AGACTCTGCA | 2460
| AAGAGAGACC | TGGGACAAC | AAGCATGAGC | ACAGGACAGC | AAGGGAGGGG | GCTGGATTGT | 2520
| GAGGAGGGAG | TGGGAGGGGG | AGAACTGACA | CAGCAGAAAC | CTCAGCTTCC | TCATCTGTAA | 2580
| AATGGGATGA | CAATCATCCC | TGCTGCCTTG | CAGAGCTGTT | GAGAGGACTG | AGTGAGAGCA | 2640
| CCATGAAGAA | TGCCTAACAC | TTGGTAGGCA | CTCAGTAGCA | AATAGTAGGT | GCTCGATTAA | 2700
| TAATCTGAGA | GGACAGATTT | GGGAGGGATT | GCAACGAGTG | CATTATCAGA | GCAGGGAGGT | 2760
| TGAAGTCGGC | CCTCAGAAGG | GTGTAGTTTG | GGGTGGGGTG | GGTCCACTTG | GGAGAGGAAG | 2820
| GAGGGAGGTG | GCGTGTGAGG | CTGTTCTGCC | CTCCTCATCC | TACTCCCTTA | CCTCTCCCAA | 2880
| CCCTTCCCTT | GCACAGACTG | AGTTTCGGGA | ATGTGACTAC | AACAAATTCA | TGAGTGTTCT | 2940
| GGACACCAAC | AAGGACTGCG | AGGTGGACTT | TGTGGAGTAT | GTGCGCTCAC | TTGCCTGCCT | 3000
| CTGTCTCTAC | TGCCACGAGT | ACTTCAAGGA | CTGCCCCTCA | GAGCCCCCCT | GCTCCCAGTA | 3060
| GCCTCTGCTC | CAGGGGTGC | GCTGGCTGTC | GGGGGCTGGG | CATGTCTCCC | ACACCCCTC | 3120
| CTACCCTCTC | TCCTGTACCC | CTTTCAATCT | GGACTTGCCC | AGGTCTTCTG | CGATCAGTTA | 3180
| ACCCATTTTA | CCTAGGAGGC | CCAGAGATGT | GAGGGCTCCT | TCCTCAGGAT | GCCCAGCGAA | 3240
| TGAGGGGTAG | AGCCACTCTG | GGCCCAGCC | TGCCTGCCGC | ACCCCTGTGG | CCTCCCTTGT | 3300
| GGATGGGAGG | AGGCGGGATC | TGCTCTGAGG | CCCTCGAGGC | TCAGCAGAGC | GTGCACCAAT | 3360
| GAGACCACGA | TGGGAAAGGG | CCTATTTAAC | TCCTAATAAA | AAACTGGCAT | CAGCTTGGTT | 3420
| TTGTTTGGTT | CTTCTCTGAG | GACGCGTCTC | CTGAGCTCTT | TGCTCCTCTC | TGGCCTTTTC | 3480
| CACTGCGGGA | AGGCAGCTGA | GGGCAGGGGC | AGGGTGCTCC | CTGAGGGAAG | TTGCAGACCC | 3540
| TGCAGAAATG | CAGTGGCCTC | CAGGGTCCAG | CAGGAGGGCG | TGGGACAAA | ACAAGGACCC | 3600

| | | | | | | |
|---|---|---|---|---|---|---|
| CTGTCCTCCC | TTCCTCTCTC | TCTTTCTTTG | GGATCTTTGA | GAGAGGACTG | CCTGAGTTTC | 3660 |
| CCCTGGGACT | CAGTGCTCAT | GGTTGGAGGA | GGGTGGGGCC | GTGGGTGCAG | TGGGGGTGTT | 3720 |
| TGTTCCCTGC | CTCGGGCTGT | GGGAGCCAG | AGAGCAGCAC | TAATGGGATT | AGGGTGTCTG | 3780 |
| AGGTGTTTCT | CCCAGCCAGG | AAGGGGTGCT | CTGTATGGAG | GGGTAAGGGA | ATAACTTGAG | 3840 |
| CTAGCCCCTA | TCCCTGAAGC | CGCAGCCCCC | TGAGGGCCTT | AACCCCCTAC | TTCTAACCCT | 3900 |
| CACTGGGTTT | GTAGCCCACC | CTGAGAGGTT | GACCCGAATT | ATAACTCCCC | TATTTCATGC | 3960 |
| CATTTCACCT | CTAACTCTCC | ACCCCAACCT | GGATTCTTCA | TTCCTGACAC | TCATCCCAAC | 4020 |
| TTTAAATGGC | CCCTCCTGAT | ACCCTCTCCG | AACCTGAGAT | CTATCCGTGA | GCCCCACGC | 4080 |
| CTCACTGCCA | CTCCACTCCA | TCACTACCTC | ACCCAGGACC | TTTCCCACTG | ACGTTCCTGA | 4140 |
| GGTGGTCCCA | GAGCCTCCTT | TGGGTGTGAG | CCTGTTCCCC | TCCAGATCCC | CCCGCCCCGA | 4200 |
| CCCTGAGCCT | TACTTGGCAT | GGCAGACAGT | ACCGGGCATG | GGATCCCCA | CCCCAGTTTT | 4260 |
| TGTTTCTGAA | TCTTTATTTT | TTTAAGAGAC | AAGGTCCTCT | GTGTTGCTCA | GGCTGGAGAG | 4320 |
| CAGTGGCTTG | AGCATAGCCA | ACTGCAGTCT | CGAACTCCTG | GGCTCAAATG | ATCCTCCTGT | 4380 |
| CTCAGCTTCC | TGACTAGCTG | GGACTACAGG | CTACAGCCAT | GCTGCCCAGC | TAATTAAAAA | 4440 |
| AAAAAATTGT | TTTTCCTTTT | TATAGAGACA | GAAGTCTCTC | TATGTTGCCT | AGGCTGGTCT | 4500 |
| TGAACTCCTG | GCCTCAGGCG | ATCCTCCCAT | CTTCCCCCTA | GCTTTTGTGT | CACCACATTT | 4560 |
| CCAGGGCAAT | CTCCCACCTG | TCACCCACCA | CCCCCTGCAT | CTTCTTTCCT | AGGTCCCCAT | 4620 |
| GGGACTACTC | CCTGTCCCCC | ATGCTCCAGG | CACAGGCTGC | CCCTTCCTCC | ACCTCTCTAA | 4680 |
| AACTCAGGCT | GAGCTATGTA | CACTGGGTGG | TGCCCATCTC | ATCCAGTCCC | CTGCTAGTAA | 4740 |
| CCGCTAGGGC | TTACCCGTTA | CCCACGGGTG | CCCACCTGGG | AACAGGAGGC | TTGGTTCCAC | 4800 |
| GGCTGGGCTG | GTGGAGGGTG | CTGTGGCACT | TACCGCATCA | GCCCACAGCA | GGAAGGCAGT | 4860 |
| ATCCGCTCTC | CCCTGTCCCC | TGCTATGGGC | AGGGCCTGGC | TGGGGTATAA | ATAGGTCAGA | 4920 |
| CCTCTGGGCC | GTCCCCATTC | TTCCCCTCTC | TACAACCCTC | TCTCCTCAGC | GCTTCTTCTT | 4980 |
| TCTTGGTTTG | GTGAGTTGTG | TTGGCCTGAC | TGGCATGCAA | GGGGTGTCAG | AGGCCAGGGC | 5040 |
| TGGGAAGGA | GAAGGGGAGG | CTGGTGGGGG | CCAGATGTGC | TAAAGAGATC | CAGATGTGAG | 5100 |
| ATTCTGATGT | GGAACTCTGG | GTGGATTGTG | TGCGTGGGTG | TGCATGGCAC | ACACACACAT | 5160 |
| GCACGTAAGA | CGGAGGAAAA | AACAAACAGA | AAAGTGAGCA | AGTGACTGAA | TTTGAGCTCT | 5220 |
| CCAGGTGCTT | CTGAGATGTG | GGCTTGCACA | CGCTGTTGCT | ATAGTACGTG | TTGGTATGTA | 5280 |
| TGTGCCTGTG | GGTATCTGCA | CTGGCTCATG | TTTGCTGGGT | TGCGCACTCG | GGAGCAGGAA | 5340 |
| GCAAAGGAAA | GGCAGAAGGC | AACTGTGGGC | CTTTGTCTGG | TGGTGTGCCC | CATGAGCCTC | 5400 |
| TGCCCTGCAC | GCAGCAGCCC | AGCTCGAGAA | GGTGCATGGC | CTCTGCAGCT | TCTCTTCCAA | 5460 |
| CCCTTGCCTC | TGCCACCTCA | CTTTGCCCCT | CCCCATGCTG | AGAGCTAAGC | GGCTGTGCTG | 5520 |
| GTTTTTTCCA | CTGCAGGCCC | CTGGGCAGGC | CTCCAGCAGC | CACACCCAGT | TCTGGGAGGG | 5580 |
| AAAAGAATGG | CAAGGGCGGG | GCCTTTGTGG | CTGAGCTGTG | GGAGTGGATA | GACTGAGTGA | 5640 |
| GGGGTGGAAA | AAATGCTGTT | GTTGAGGCAA | GGCCTGGGAG | GCCCTGGGAG | TTTGCTGCCC | 5700 |
| GAATCTCCAG | AGCTTGCGCA | GCGGATCTTG | CAAATGTTCA | CTGCCCAGAG | CATGTGTTCC | 5760 |
| CCACTGTGCA | CACCCTCCCA | GCCAGGTGCG | GGGCCCACT | GCTCTGGGCT | CCCCCAGGGA | 5820 |
| GGGAGCAGAG | TCTCGCCAAG | TGCTCCTGGA | GGGATGGGAG | TGGAGCCTGG | CATTCTGAAC | 5880 |
| ACATCTCTGA | GGGGTGGGAT | TAATAAGACG | GTCTCTGTGC | CTCCTGCTCC | CAGATCCTGA | 5940 |
| CTGCTGTCAT | GGCGTGCCCT | CTGGAGAAGG | CCCTGGATGT | GATGGTGTCC | ACCTTCCACA | 6000 |

| | | | | | | |
|---|---|---|---|---|---|---|
| AGTACTCGGG | CAAAGAGGGT | GACAAGTTCA | AGCTCAACAA | GTCAGAACTA | AAGGAGCTGC | 6060 |
| TGACCCGGGA | GCTGCCCAGC | TTCTTGGGGG | TGAGTGGGTA | GTGCCTGAGT | GAGTCCCCAC | 6120 |
| GTGGGGCATT | TCCCACAGAG | GAGGGCAGCA | GTCTTGCTCT | AGAGCATTAG | CTACAGAGGG | 6180 |
| CATCTATCAG | TGGGGTGGCT | GCCTGGGGTG | GAAACACATT | GAACACCACC | ACTCACTGCC | 6240 |
| TGGCCCCATG | CTGAAAGAGG | GCTGAGAATG | AATGGGTCAG | ACACTGCCAG | GTGCTTTGCA | 6300 |
| CAACTTAACT | GAAGGGAAGA | CTAAGCTCAG | AGTGCTAAGT | AACTTCCCAA | GGTGGTCAGT | 6360 |
| GTACACAACT | GCCATCCGGA | CCGGGACTGT | CTGACTCTTG | CCATCACTCC | AACAGTGGAC | 6420 |
| ACTGTTTGAG | TTTCTATTTG | GCTTGTAGAT | GTGAAGACAC | AGATGTGGAG | ATGATCACAG | 6480 |
| GCCTGCAGAC | GTTCCCTTCA | AACAATAACA | ATGTATATTT | GTATCAAACA | TAACACAGTT | 6540 |
| TATATATTGT | TTTCATGACT | ATTACTACCT | CATGGGATTA | TTAGAACAAC | CTTGGGTGAA | 6600 |
| AATGTAGTGG | TCCCGTCATT | TTTCCATTGC | ACCAGGTACT | CAGACTTCCT | TATCCAAGGA | 6660 |
| GCACCTTCTC | CACCCTAGCT | TAGCCTTGAG | GGTTGGAGTT | CCAAACTGGA | CCTCCCAAAG | 6720 |
| GAGCCTCCCT | GAACTCTGGT | CTGGGAGTAG | AAACTGGGTC | TGGTCCTGGC | TCCACCCACT | 6780 |
| GGGCTTCTGT | TTTCTATCTG | TAGCCTCTTC | TCCCTCCAGA | AAAGGACAGA | TGAAGCTGCT | 6840 |
| TTCCAGAAGC | TGATGAGCAA | CTTGGACAGC | AACAGGACA | ACGAGGTGGA | CTTCCAAGAG | 6900 |
| TACTGTGTCT | TCCTGTCCTG | CATCGCCATG | ATGTGTAACG | AATTCTTTGA | AGGCTTCCCA | 6960 |
| GATAAGCAGC | CCAGGAAGAA | ATGAAAACTC | CTCTGATGTG | GTTGGGGGGT | CTGCCAGCTG | 7020 |
| GGGCCCTCCC | TGTCGCCAGT | GGGCACTTTT | TTTTTTCCAC | CCTGGCTCCT | TCAGACACGT | 7080 |
| GCTTGATGCT | GAGCAAGTTC | AATAAAGATT | CTTGGAAGTT | TTGAGGCTGA | TGGTTTGAGA | 7140 |
| GACTCTGGGG | GCGTGGGTTG | GGGACTGAGG | GATATGTTGT | GGGGTGGTGG | TGGGAGAGC | 7200 |
| TGGGAGTTGA | GCTGAAGTTT | TATGGACAGC | AGACCAGTGA | AGTTAGGGGA | GGGATGCAGG | 7260 |
| GTGACTAACA | GTGTGTGTGC | ACAGGCAATA | GAGTTCACTC | GGTGTGGTCA | AAGCCGAGAA | 7320 |
| GGGGACCCTC | ACCACCCCCT | GCCAAGGTTT | GGAAGGTCCA | GCTGTGGGAT | CTCAGCCAGC | 7380 |
| CCACTTACCC | CTCCCACCTC | TCTCCAACCT | TGCCTCTGGC | AGGATCTTGA | ACCGAGGCTG | 7440 |
| GAATTGAAGG | TCATATCTGT | TCCTGGTTGG | GGTCTGGAAT | GGAGTTTGGG | TGTCCTGGGA | 7500 |
| GTAAGTCGGA | GGGAAAAGAA | TAAGGCTGAG | TTGCAGGGAG | GAAGTATTTA | GGCGAGAGTG | 7560 |
| GGATGGGGAG | GAGGGCTGGC | ACTCAGTGCT | GACGTTGACA | GTCCAGGCCC | TGTCCTGCCA | 7620 |
| CCCACTTCCA | GATCATTGGC | TTCAAACCAC | AGGGATGGAT | TAATCCTTTC | CTGTGCGTGG | 7680 |
| TAGGATCAGG | GAGGGCAATG | TGGAGGGAGA | CCCGCTGTTT | GCAGCAGCAT | GAGAATATAG | 7740 |
| GCATTCTCGA | ATCCACCGTC | TCTGCCATAA | AGGTCCCTGG | ATGAGATCTG | TTATCAGTCA | 7800 |
| GGAATCAAGC | TCCTTCAGAG | AAGGACAGGG | GACCTCAGAA | GAGATGAGTG | GGGGTCAGTG | 7860 |
| GCTGGAGTGG | GAGTGAGGCA | AATGGTGGGA | AGGTGACCAT | AGTTTTGGAG | ACAAAATTCC | 7920 |
| ACATATATGA | TCTGACAAAT | GAAATTGAGA | TTATTTTCCC | CCCAGAAAAT | ATAAGGCATG | 7980 |
| ATATTGCTTC | CCCTTAGGTA | GGTTCAAGGC | CAGTGGCTCC | AGGGTGCAGT | GGTGGGTTGA | 8040 |
| GGTTAGACTT | CAAGGCCATG | TCTGGGTGAC | TCAGGGATCA | CTTTTTAGGA | AGAGGTGGCA | 8100 |
| TGGAGGTCAG | GTGGCAGAGG | GCTGGAGGGC | TTTGTCCCAC | TGACCTCCTC | TTGAGGGTCC | 8160 |
| TCTTTCCTCT | CATCACATGG | GGCTTTTCTC | TCAGGTTTCA | GAGGAGTGGG | GCAGGTGACT | 8220 |
| CAGATGTTCC | CGCAGGGTTT | GAATACAGAG | ACTTGGGAGG | AATTTCAGTT | CAGGAGAAAG | 8280 |
| TCTGCTGCCT | TCCGCTGCCC | TCTCCATCCA | CCCTCCCTGG | GAGGGCCCTT | CCTGGGGCCT | 8340 |
| CCACCCAGGT | CACGCTCTCC | TTCAGAGATG | CCTACTGCAT | AGCAACCAAT | CCCTGCTGCC | 8400 |

| | | | | | | |
|---|---|---|---|---|---|---|
| TCTCCAATCT | TGCCAGCTGG | GGGTGGGGTG | GAGTGGGGAG | CAGTGGGGAG | GCCCCCCAGG | 8460 |
| CTGGGGTGGG | ACTGCAGCAG | TGATAGGTAC | TACACCCTGA | GCCCAGGTCT | GTTCTTGGAC | 8520 |
| TGGTGGTAGA | AGTATGTTGT | TCTACTGTGG | TAGAACGATG | TCTGAGTGTC | TCCTGGGATA | 8580 |
| CAGGAAACTC | TCCCTGGCCC | CTACTTCCTC | CTTGACTGCA | GCCTGAACCT | GAACCCCCCT | 8640 |
| CCCCAATCCA | CAACCTCTAC | CCCAGTGCTG | GGCCTTAGCC | CTTCGCTGGA | CACCTTCCCT | 8700 |
| ATTCCTGATT | CTCAGTCCTC | CATGCCAAGA | GTCTCCGACG | AGCCTTTCCT | GTGAAGAGCA | 8760 |
| GTGAGGCCTA | GAAGAAATCG | TTCATTTAAA | AGCCCTTTAA | AAACCTCTGG | GCCCATATTA | 8820 |
| GCTCATGACC | TTGACCATAT | CCTTCGCAGA | AAATATCTTC | CTCCACTGAT | CCCCATCTCA | 8880 |
| AGGGCTGTCT | TCTCTACTCC | TGGAGTGGGT | GGCAGGATGG | GTGGGAGGGG | CCCGATGTGG | 8940 |
| AGAGCTTCCT | AGGACACGGG | GAGATGGTGC | CCTGTGTTTG | TCCCACACTT | CTGAGGTTTT | 9000 |
| CTTTCCAGGA | CAGCCTGGTT | TCCCTTCTTC | GGCTTATTGT | TCCATCAGAT | TTCAGATTTT | 9060 |
| GAGTTCTGAT | TTTTGGTCAG | AAGAGTAAAG | TTTCTGGGAT | TGGGGACGTG | TGTGCTATGG | 9120 |
| GAACTCAGTG | TGTCCCCAGC | CCTTGTTTGT | AAACAAGGAA | GGTGAGATTG | GCAGAAGGGG | 9180 |
| TTTCTCCCCA | GCTCCATCCC | GGGAGGCTCT | GACGTGGGCA | TCCTCAAGTC | CCCAACAACT | 9240 |
| TCTCATGGGC | CCTTTCTCTC | CCCTGGATTC | CTAGGGACAG | AGATCAGGGA | AATAAAGGCA | 9300 |
| GAAGGCAGTG | AGAGGGAGGC | TATGCCTGCT | GCTTGGATTC | TCTGGGCTCA | CTCCCACAGT | 9360 |
| GGTAAGTCCT | TCCTTCCTAT | GTCTCTGTTC | ATCTGATATC | TGGTGGGTCA | CGCTGGATGA | 9420 |
| TGAGGGTGAC | AAGTGGTGGT | GACCTCCACC | AAGGAGGCCT | GGCCCCACAA | GCGGGCATGC | 9480 |
| GCTCAGGGAG | AAGAGGGCAG | AGCCTTTGGA | ATTTCTTGAG | AAATGGCTCT | GGGGTGGAGG | 9540 |
| TGGGGGTCTG | GACTAGCCAG | GATGCTCCTG | CAGGTGCACA | GAGTCCCTTG | CCTTCAACTG | 9600 |
| TGGTCCCAGC | TGAGTCTCCT | TGAGGTGGGA | GAGGCTGAGG | TTTTTGTGGT | GGGAGAGGAA | 9660 |
| TGATGGGTCT | GGTTCAAGAA | TGGCAGGGAG | GGCTTTGGGC | TGGAGGTGAA | GACTCTCCAC | 9720 |
| AGATTTAACC | TGCAGCCTTC | AAGTTCCGTG | GGTGTTGCCT | CCTTCCTCCC | TGAGGGGGAA | 9780 |
| GTGGTTTTTG | AGTCTGAGTC | ACTTGAGCTC | CATCTGTCTC | TTCCCCTTGG | CTGAGGGTGG | 9840 |
| CTGTGCTATT | GGAATCCAGG | CCCTTATTCA | AGCGTAGCCT | CTGGATCCAG | GTTTTGGAAT | 9900 |
| GATCCTGGAG | ATTTCAAGAG | GCCCCTGCC | CTCCTGCCC | GCTGACCCGT | CTCTGTGTGC | 9960 |
| ACTGCTCTGG | GCCAGAGTCT | GGAGACCAGC | TGGGCCAGCT | CAGCTCACCT | CCCTGCTGCT | 10020 |
| CCTTGTTGAG | ACCCCATCAC | CCAGTTCCAG | CCCAGCCCCC | TCTCAGCCCT | GGACTCTCTC | 10080 |
| TTTGCCCTGT | CCCCGACTTT | AATAATGGGA | CACTCCTCGA | TATCAGGTGA | TTCAGGCACT | 10140 |
| GGGGGAAAGG | CTGGTGAACT | GCCTGTGGAA | AACCAGTTCC | TAAGCTGGAA | GAAGCAGAGA | 10200 |
| GAAAATCGTG | ACCCTTGATC | TGCTCCACCA | TCTGCCACCA | GGCCTTTTGA | GGAGGTCGTC | 10260 |
| TTCTCATCTT | TCTGCCTCAG | GCCTACTTTT | CAACAACTCC | CCAGCAGGAG | AGTCTGTGGT | 10320 |
| CTCCTTTGGG | GTCTTGCTGT | TCTCCTTGTA | CCAGCAGCTC | CAGAGTTTGT | TGTGGGTCTC | 10380 |
| ATGGTAACCT | GTACTGATAT | AGATGGGCGC | TCTTGTTAGT | GGATTTCAGT | CTCATCCTGG | 10440 |
| GTTCCAGTCT | CTTGTTCTTT | GAGGGAGGGG | CCTCAGAGGT | AGGCTAGTGC | TGCTGGTGGT | 10500 |
| GACTTCCTGA | GGAATGGGAT | CTTCCCCTCT | CCCTCTACAG | AGCTGCACAC | TGTGATGGAG | 10560 |
| ACTCCTCTGG | AGAAGGCCCT | GACCACTATG | GTGACCACGT | TTCACAAATA | TTCGGGGAGA | 10620 |
| GAGGGTAGCA | AACTGACCCT | GAGTAGGAAG | GAACTCAAGG | AGCTGATCAA | GAAAGAGCTG | 10680 |
| TGTCTTGGGG | AGGTAGGTGA | TTGTTCCCTC | ATCCTCCACC | CCAAAGTCTG | AGTACTCCCT | 10740 |
| CTGGGGGACA | CATACCTACC | CTCAGGATCC | TCCAGCCTAA | GCCAGGGCA | GGGTGGCCAA | 10800 |

| GGGCTACAGA | CAGAGACAAA | GGAAGATGGT | GGGGATTTCG | GGCCAGCAAA | ACTCTAGCCC | 10860 |
| TCTGTGAAGG | AGAATGGGTC | AGGGTCTCAC | TGAGAAGGAG | GAAGGGCTGA | GTCTGGAGGG | 10920 |
| TTTAGAGAAG | GAGATTGAGG | AGCCTTCGAT | GG | | | 10952 |

( 2 ) INFORMATION FOR SEQ ID NO:2:

( i ) SEQUENCE CHARACTERISTICS:
        ( A ) LENGTH: 3 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:2:

GUC    3

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

GTCAGGATCT GGGAGCAGGA GG    22

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: RNA ( i i i ) HYPOTHETICAL: NO ( i v ) ANTI-SENSE: NO ( x i ) SEQUENCE DESCRIPTION: SEQ ID NO:4:

GUCAGGAUCU GGGAGCAGGA GG    22

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

CACAACTCAC CAAACCAAGA AA 22

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: RNA (iii) HYPOTHETICAL: NO (iv) ANTI-SENSE: NO (xi) SEQUENCE DESCRIPTION: SEQ ID NO:6:

CACAACUCAC CAAACCAAGA AA 22

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

CAGAGGGCAC GCCATGACAG C 21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

CAGAGGGCAC GCCAUGACAG C 21

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

GGAAGGTGGA CACCATCACA 20

(2) INFORMATION FOR SEQ ID NO:10:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: cDNA/RNA ( i i i ) HYPOTHETICAL: NO ( i v ) ANTI-SENSE: NO ( x i ) SEQUENCE DESCRIPTION: SEQ ID NO:10:

GGAAGGTGGA CACCAUCACA                                                         20

( 2 ) INFORMATION FOR SEQ ID NO:11:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

TCGACTGGAA GGTGCTGATG AGTCCGTGAG GACGAAACAC CATCACAA                           48

( 2 ) INFORMATION FOR SEQ ID NO:12:

( i ) SEQUENCE CHARACTERISTICS:
    ( A ) LENGTH: 48 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

AGCTTTGTGA TGGTGTTTCG TCCTCACGGA CTCATCAGCA CCTTCCAG                           48

( 2 ) INFORMATION FOR SEQ ID NO:13:

( i ) SEQUENCE CHARACTERISTICS:
    ( A ) LENGTH: 43 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:13:

TTGTAATACG ACTCACTATA GGGTGGAAGG TGCTGATGAG TCC                                43

( 2 ) INFORMATION FOR SEQ ID NO:14:

( i ) SEQUENCE CHARACTERISTICS:
    ( A ) LENGTH: 22 base pairs
    ( B ) TYPE: nucleic acid

```
              ( C ) STRANDEDNESS: single
              ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:
```

TGTGATGGTG TTTCGTCCTC AC                                                    22

( 2 ) INFORMATION FOR SEQ ID NO:15:

```
    ( i ) SEQUENCE CHARACTERISTICS:
              ( A ) LENGTH: 43 base pairs
              ( B ) TYPE: nucleic acid
              ( C ) STRANDEDNESS: single
              ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:15:
```

TTGTAATACG ACTCACTATA GGGACAACCC TCTCTCCTCA GCG                             43

( 2 ) INFORMATION FOR SEQ ID NO:16:

```
    ( i ) SEQUENCE CHARACTERISTICS:
              ( A ) LENGTH: 20 base pairs
              ( B ) TYPE: nucleic acid
              ( C ) STRANDEDNESS: single
              ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:
```

GGGCAAAGAG GGTGACAAGT                                                       20

( 2 ) INFORMATION FOR SEQ ID NO:17:

```
    ( i ) SEQUENCE CHARACTERISTICS:
              ( A ) LENGTH: 19 base pairs
              ( B ) TYPE: nucleic acid
              ( C ) STRANDEDNESS: single
              ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:17:
```

AGCACAGAGC CTCGCCTTT                                                        19

( 2 ) INFORMATION FOR SEQ ID NO:18:

```
    ( i ) SEQUENCE CHARACTERISTICS:
              ( A ) LENGTH: 17 base pairs
              ( B ) TYPE: nucleic acid
              ( C ) STRANDEDNESS: single
              ( D ) TOPOLOGY: linear ( i i ) MOLECULE TYPE: cDNA
```

(iii) HYPOTHETICAL: NO (iv) ANTI-SENSE: NO (xi) SEQUENCE DESCRIPTION: SEQ ID NO:18:

TGGATCCCTC GAAGCTT                                                                                              17

(2) INFORMATION FOR SEQ ID NO:19:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:19:

CTCACGGACT CATCAGC                                                                                              17

(2) INFORMATION FOR SEQ ID NO:20:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:20:

ACAACCTCT CTCCTCAGCG                                                                                            20

(2) INFORMATION FOR SEQ ID NO:21:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:21:

GGGCAAAGAG GGTGACAAGT                                                                                           20

(2) INFORMATION FOR SEQ ID NO:22:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (iii) HYPOTHETICAL: NO (iv) ANTI-SENSE: NO ( x i ) SEQUENCE DESCRIPTION: SEQ ID NO:22:

GCCATGACAG CATGCAGGAT 20

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( x i ) SEQUENCE DESCRIPTION: SEQ ID NO:23:

GTCAGGATCT GGGAGCAGGA G 21